US011318231B2

(12) United States Patent
Veiseh et al.

(10) Patent No.: US 11,318,231 B2
(45) Date of Patent: May 3, 2022

(54) ANTI-INFLAMMATORY COATINGS TO IMPROVE BIOCOMPATIBILITY OF NEUROLOGICAL IMPLANTS

(71) Applicants: Massachusetts Institute of Technology, Cambridge, MA (US); Seattle Children's Hospital, Seattle, WA (US)

(72) Inventors: Omid Veiseh, Bellaire, TX (US); Robert S. Langer, Newton, MA (US); Daniel G. Anderson, Framingham, MA (US); William Shain, Kirkland, WA (US); Brian W. Hanak, Seattle, WA (US); Samuel R. Browd, Mercer Island, WA (US); Robert F. Hevner, La Jolla, CA (US)

(73) Assignees: MASSACHUSETTS INSTITUTE OF TECHNOLOGY, Cambridge, MA (US); SEATTLE CHILDREN'S HOSPITAL, Seattle, WA (US)

( * ) Notice: Subject to any disclaimer, the term of this patent is extended or adjusted under 35 U.S.C. 154(b) by 175 days.

(21) Appl. No.: 16/182,307

(22) Filed: Nov. 6, 2018

(65) Prior Publication Data

US 2019/0134277 A1    May 9, 2019

Related U.S. Application Data

(60) Provisional application No. 62/582,126, filed on Nov. 6, 2017.

(51) Int. Cl.
| | | |
|---|---|---|
| *A61K 31/192* | (2006.01) | |
| *A61L 29/08* | (2006.01) | |
| *A61L 29/16* | (2006.01) | |
| *G01N 33/68* | (2006.01) | |
| *A61L 31/06* | (2006.01) | |
| *A61L 27/34* | (2006.01) | |
| *A61L 29/06* | (2006.01) | |
| *A61L 31/10* | (2006.01) | |
| *A61L 31/16* | (2006.01) | |
| *A61L 27/18* | (2006.01) | |
| *A61L 27/54* | (2006.01) | |
| *A61M 27/00* | (2006.01) | |

(52) U.S. Cl.
CPC .............. *A61L 29/08* (2013.01); *A61L 27/18* (2013.01); *A61L 27/34* (2013.01); *A61L 27/54* (2013.01); *A61L 29/06* (2013.01); *A61L 29/085* (2013.01); *A61L 29/16* (2013.01); *A61L 31/06* (2013.01); *A61L 31/10* (2013.01); *A61L 31/16* (2013.01); *A61L 2300/41* (2013.01); *A61L 2400/18* (2013.01); *A61L 2420/02* (2013.01); *A61M 27/002* (2013.01); *A61M 2205/0238* (2013.01)

(58) Field of Classification Search
CPC .......... A61L 29/08; A61L 27/18; A61L 27/34; A61L 27/54; A61L 29/085; A61L 29/16; A61L 31/06; A61L 31/10; A61L 31/16
See application file for complete search history.

(56) References Cited

U.S. PATENT DOCUMENTS

| | | |
|---|---|---|
| 2,881,161 A | 4/1959 | Kohler |
| 2,860,130 A | 11/1985 | McNeely |
| 5,336,668 A | 8/1994 | dellaValle |
| 5,443,505 A | 8/1995 | Wong |
| 5,622,718 A | 4/1997 | Al-Shamkhani |
| 5,876,452 A | 3/1999 | Athanasiou |
| 6,159,531 A | 12/2000 | Dang |
| 2003/0113478 A1 | 6/2003 | Dang |
| 2004/0253532 A1 | 12/2004 | Wu |
| 2008/0003250 A1 | 1/2008 | Margulies |
| 2008/0044900 A1 | 2/2008 | Mooney |
| 2008/0177021 A1 | 7/2008 | Berlin |
| 2008/0199914 A1 | 8/2008 | Skjak-Braek |
| 2008/0242738 A1 | 10/2008 | Marks |
| 2008/0268189 A1 | 10/2008 | Sun |
| 2009/0148591 A1 | 6/2009 | Wang |
| 2009/0197791 A1 | 8/2009 | Balastre |
| 2011/0111004 A1 | 5/2011 | Barbieri |
| 2011/0319569 A1 | 12/2011 | Emrick |
| 2012/0009159 A1 | 1/2012 | Humayun |
| 2012/0041546 A1 | 2/2012 | Belcheva |
| 2012/0083767 A1 | 4/2012 | Gerstenblith |
| 2012/0121657 A1 | 5/2012 | Zhou |
| 2012/0282299 A1 | 11/2012 | Delamarre |

(Continued)

FOREIGN PATENT DOCUMENTS

| | | |
|---|---|---|
| CN | 101565469 | 10/2009 |
| DE | 102005049833 | 4/2007 |

(Continued)

OTHER PUBLICATIONS

DeVos, et al., "Improved biocompatibility but limited graft survival after purification of alginate for microencapsulation of pancreatic islets", Diabetologia, 40(3):262-270 (1997).
Pedraza, et al., "Macroporous three-dimensional PDMS scaffolds for extrahepatic islet transplantation", Cell Transplantation, 22:1123-1135 (2013).
Tang, et al., "Reprogramming liver-stem WB fcells into functional insulin-prodcuing cells by persistent expression of Pdx1-and Pdx1-VP16 mediated by lentiviral vectors", Lab Invest 86(1)83-93 (2006).

(Continued)

*Primary Examiner* — Alma Pipic
(74) *Attorney, Agent, or Firm* — Pabst Patent Group LLP

(57) ABSTRACT

Neurological implants whose surfaces have been chemically and covalently modified to impart beneficial properties to the neurological implants are described. The neurological implants possess improved biocompatibility compared to a corresponding neurological implant that lacks the chemical modification. Following implantation in a subject, the surface-modified neurological implants induce a lower-foreign body response, compared to a corresponding unmodified product.

31 Claims, 1 Drawing Sheet

(56) References Cited

U.S. PATENT DOCUMENTS

| | | |
|---|---|---|
| 2013/0149351 A1 | 6/2013 | Lee |
| 2013/0224276 A1 | 8/2013 | Hunter |
| 2015/0183939 A1 | 7/2015 | Lequeux |
| 2015/0368713 A1 | 12/2015 | Bharti |
| 2016/0019391 A1 | 1/2016 | Ghosh |
| 2016/0030360 A1 | 2/2016 | Vegas |
| 2017/0014776 A1 | 1/2017 | Li |
| 2017/0226232 A1 | 8/2017 | Vegas |
| 2017/0239397 A1 | 8/2017 | Vegas |
| 2017/0246347 A1 | 8/2017 | Vegas |

FOREIGN PATENT DOCUMENTS

| | | |
|---|---|---|
| EP | 1614696 | 1/2006 |
| FR | 2699545 | 6/1994 |
| GB | 676618 A | 7/1952 |
| GB | 768309 | 2/1957 |
| WO | 9900070 | 1/1999 |
| WO | 2003010354 | 2/2003 |
| WO | 2003085372 | 10/2003 |
| WO | 2005058382 | 6/2005 |
| WO | 2005063147 | 7/2005 |
| WO | 2009032158 | 3/2009 |
| WO | 2010090767 | 8/2010 |
| WO | 2012167223 | 12/2012 |
| WO | 2013121983 | 8/2013 |
| WO | 2014044697 | 3/2014 |
| WO | 2014052080 | 4/2014 |
| WO | 2015054484 | 4/2015 |
| WO | 2015187204 | 12/2015 |
| WO | 2016019391 | 3/2017 |
| WO | 2017075630 | 5/2017 |
| WO | 2017218507 | 12/2017 |

OTHER PUBLICATIONS

Anderson, et al., "Conotoxins: Potential weapons from the sea", J. Bioterr. Biodef., 3:120 (2012).
Pedraza, et al., "Preventing hypoxia-induced cell death", PNAS, 109(11):4245-4250 (2012).
Kovach, et al., "The Effects of PEG-based surface modification of PDMS microchannels on long-term hemocompatibility", J. of Biomedical Research Pt. A, 102A:4195-4205 (2014).
Ratner, "A pore way to heal and regenerate: 21st century thinking on biocompatibility", Regenerative Biomaterials, 107-110 (2016).
Biran, et al., "Neuronal cell loss accompanies the brain tissue response to chronically implanted silicon microelectrode arrays", Exp Neurol., 195(1):115-126 (2005).
Chen et al., "Multifunctional Biocompatible Membrane and it's application to fabricate a miniaturized glucose sensor with potential for us in vivo", Biomedical Microdevices, 1(2):155-166 (1998).
Chen, "Differentiation of rat marrow mesenchymal stem cells into pancreatic islet beta-cells", World Journal of Gastroenterology, 10(20): 3016-3020 (2004).
Chen, et al., "Novel Zwitterionic Copolymers with Dihydrolipoic Acid: Synthesis and Preparation of Nonfouling Nanorods", Macromolecules, 46:119-27 (2013).
Chu, et al., "A soft and flexible biosensor using phospholipid polymer for continuous glucose monitoring", Biomedical Microdevices, 11(4): 837-842 (2009).
Costa, et al., "Covalent immobilization of antimicrobial peptides (AMPs) onto biomaterial surfaces", Acta Biomaterialia, 7(5): 1431-1440 (2010).
Cui, et al., "Electrochemical deposition and characterization of poly(3,4-ethylenedioxythiopene) on neural microelectrode arrays", Sensors and actuators B: Chemical: International Journal Devoted to Research and Development of Physical and Chemical Transducers, 89(1-2): 92-102 (2003).
Dai, "Swelling characteristics and drug delivery properties of nifedipine-loaded pH sensitive alginate-chitosan hydrogel beads", Journal of Biomedical Materials Research Part B: Applied Biomaterials, 86(2):493-500 (2008).

Desai, et al., "Advances in islet encapsulation technologies", Nature Reviews, Drug Discovery, 16(5):338-350 (2016).
Dusseault, "Evaluation of alginate purification methods: effect on polyphenol, endotoxin, and protein contamination", J Biomed Mater Res A., 76(2):243-251 (2006).
Extendend European Search Report issued for EP 18 16 2427 dated Jun. 19, 2018.
Gattas-Asfura, "Chemoselective cross-linking and functionalization of alginate via Staudinger ligation", Biomacromolecules, 10:3122-3129 (2009).
Hall, "Microencapsulation of islets within alginate/poly(ethylene glycol) gels cross-linked via Staudinger ligation", Acta Biomaterialia, 7:614-624 (2011).
Hersel, et al., "RGD modified polymers: biomaterials for stimulated cell adhesion and beyond", Biomaterials, 24(24):4385-4415 (2003).
Hudalla, et al., "Immobilization of peptides with distinct biological activities onto stem cell culture substrates using orthogonal chemistries", Langmuir, 26(9):6449-6456 (2010).
Huh et al., "From 3D cell culture to organs-on-chips" Trends in Cell Biology, 21(12):745-754 (2011).
International Search Report PCT/US2018/059393 dated Feb. 18, 2019.
Kozai, et al., "Brain tissue responses to neural implants impact signal sensitivity and intervention strategies", ACS Chem. Neurosci., 6:48-67 (2015).
Lee, et al., "Development and characterization of an alignate-impregnated polyester vascular graft", Journal of Biomedical Materials Research, 36(2):200-208 (1997).
Leung, et al., "Characterization of microglial attachment and cytokine release on biomaterials of differing surface chemistry", Biomaterials, 29:3289-3297 (2008).
Pedraza, "Engineering an optimal bioartificial pancreas for islet transplantation using bioactive scaffolds", Dissertation (Ph.D.) University of Miami, (2011).
Prodanov, et al., "Mechanical and Biological Interactions of Implants with the Brain and Their Impact on Implant Design", Front. Neurosci., 10(11 ):1-20 (2016).
Skousen, et al. "A strategy to passively reduce inflammation surrounding devices implanted chronically brain tissue by manipulating device surface permeability", Biomaterials, 36:33-43 (2015).
Skrzypek, et al., "Pancreatic islet macroencapsulation using microwell porous membranes", Scientific Reports, 7(1) (2017).
Sun et al., "Funcitonalization of quantum dots with multidentate zwitterionic ligands: impact on cellular interactions and cytotoxicicty", Journal of Materials Cemistry B, 1(44):6137 (2013).
Thevenot, et al., "Surface chemistry infulences implant biocompatibility", Current topics in Medicinal Chemistry, 1-21 (2011).
Valle, et al., "Synthesis and rheological properties of hydrogels based on amphilic alginate-amide derivatives", Carbohydrate Research, 344(2):223-228 (2009).
Vegas, et al., "Combinatorial hydrogel library enables identification of materials that mitigate the foreign body response in primates", Nat Biotechnol., 34(3):345-52 (2016).
Wang et al., "Significantly reduced absorption and activation of blood components in a membrane oxygenator system coated with crosslinkable zwitterionic copolymer", ACTA Biomaterialia, 40(8):153-161 (2016).
West et al., "The biocompatibility of crosslinkable copolymer coatings containing sulfobetaines and phosphobetaines", Biomateri, 25(7-8): 1195-1204 (2004).
Wikstrom, et al., Alginate-base microencapsulation of retinal epithelial cell line for cell therapy, Biomaterials, 29:869-876 (2008).
Yang et al., "Zwitterionic poly(carboxybetaine) hydrogels for glucose biosensors in complex media", Biosensors and Bioelectronics, 26(5): 2454-2459 (2011a).
Yang, et al., "Research progress on chemical modification of alginate: A review", Carbon. Polym., 84(1):33-9 (2011).
Yesilyurt, et al., "A Facile and Versatile Method to Endow Biomaterial Devices with Zwitterionic Surface Coatings", Advanced Healthcare Materials, 6(4): 2192-2640 (2016).
Klock, "Biocompatibility of mannuronic acid-rich alginates", Appl Microbiol Biotechnol, 40:638-643 (1994).

(56) References Cited

OTHER PUBLICATIONS

Ahad, et al., "Surface modification of polymers for biocompatibility via exposure to extreme ultraviolet radiation", Society for Biomaterials, 3296-3310 (2013).
Gulino, et al., "Tissue Response to Neural Implant: The Use of Model Systems Toward New Design Solutions of Implantable Microelectrodes", Frontiers in Neuroscience, 13:689:1-24 (2019).
Belikov, et al., Pharmaceutical Chemistry, Moscow, Higher School, 43-47 (1993).
Chem. Europe "Hexazine", httpss://www.chemeurope.com/en/encylopedia/Hexazine.html, 2 pages, retrieved from Internet Nov. 4, 2020.
Lee, et al., "An aqueous=Based surface Modification of Poly(dimethylsiloxane) with Poly(ethylene glycol) to Prevent Biofouling", Langmuir, 21:11957-11962 (2005).
Yimin, et al., "Alginic Acid", China Light Industry Press Ltd., 137-140 (2008).
Ye, et al. "Physical cross-linking Starch-Based Zwitterionic Hyrdrogel Exhibiting Excellent Biocompatibility, Protein Resistance, and Biodegradability", ACS Appl. Mater. Interfaces, 8:15710-15723 (2016).

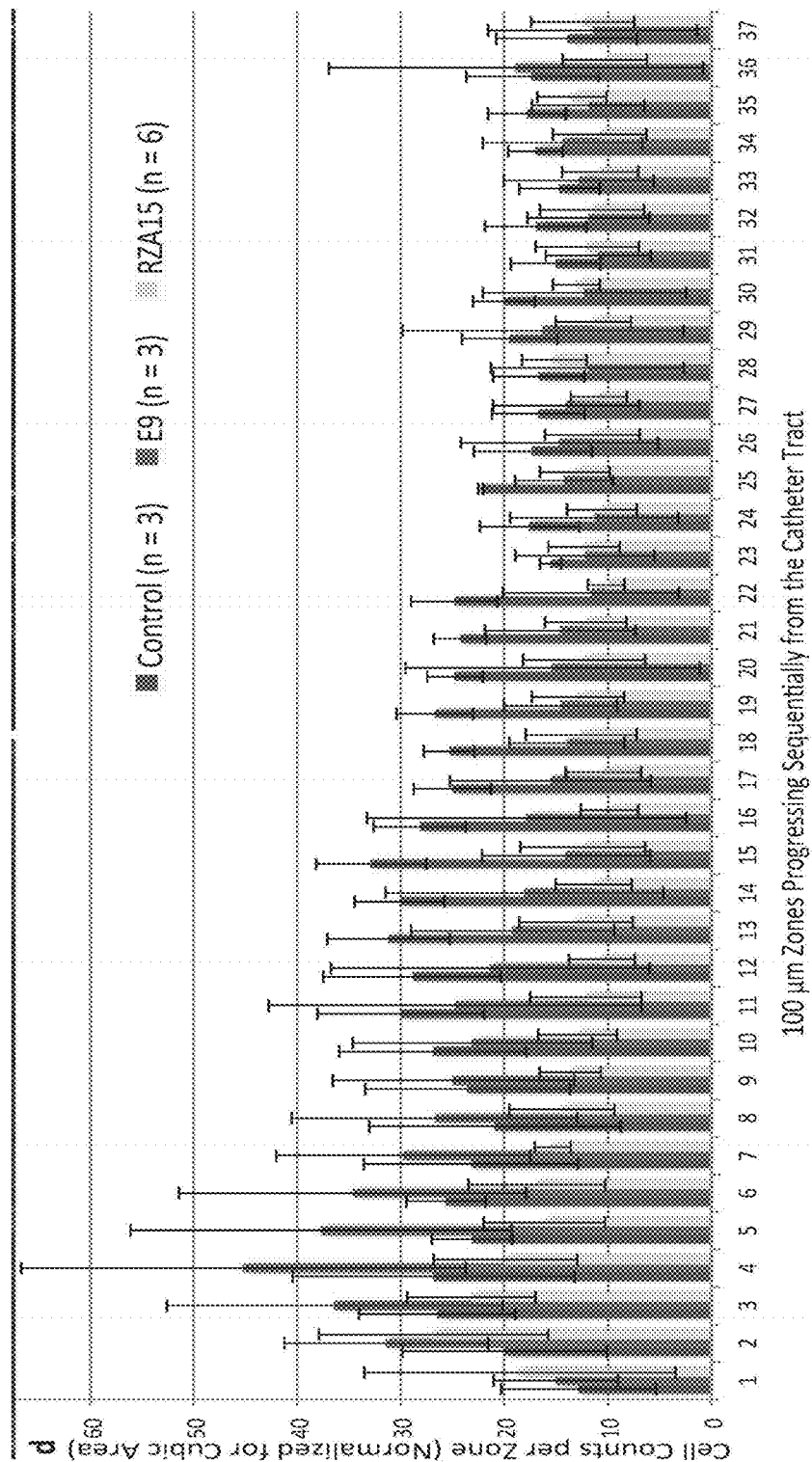

ANTI-INFLAMMATORY COATINGS TO IMPROVE BIOCOMPATIBILITY OF NEUROLOGICAL IMPLANTS

CROSS-REFERENCE TO RELATED APPLICATIONS

This application claims benefit of U.S. Provisional Application No. 62/582,126 filed Nov. 6, 2017, which is incorporated herein by reference in its entirety.

STATEMENT REGARDING FEDERALLY SPONSORED RESEARCH

This invention was made with government support under Grant W81XWH-13-1-0215 awarded by the Department of Defense (DOD). The government has certain rights in the invention.

FIELD OF THE INVENTION

This invention is in the field of implantable devices with improved biocompatibility, particularly neurological implants completely or partially coated with chemical moieties that confer improved biocompatibility, e.g., reduced inflammatory responses.

BACKGROUND OF THE INVENTION

Neurological implants are generally devices that are used to restore, replace, or bypass lost neurological functions due to disease or injuries to parts of the nervous system, e.g., the central nervous system (CNS). They provide the most value when performance is maintained for protracted periods of time (Kozai, et al., ACS Chem. Neurosci. 2015, 6, 48-67). However, the implantation of these devices into the CNS is often problematic, because of insertion injuries which activates a foreign body response. For instance, the blood-brain barrier is disrupted during device insertion, giving rise to molecular and cellular responses to neurological implants (Kozai, et al., ACS Chem. Neurosci. 2015, 6, 48-67). Another detrimental effect is the reduction and/or demyelination of local nerve fibers and neuronal cell bodies (Biran, et al., Exp Neurol. 2005; 195:115e26; Skousen, et al., Biomaterials 2015, 36, 33-43). These biochemical responses to neurological implants negatively impact performance, lead to device failure of the devices over both acute (seconds to minutes) and chronic periods (weeks to months). (Kozai, et al., ACS Chem. Neurosci. 2015, 6, 48-67).

Immediately following the insertion of neurological implants into the brain, microglia cells within about 130 μm from the site of implantation are activated, and start projecting lamellipodia towards the implant. (Kozai, et al., ACS Chem. Neurosci. 2015, 6, 48-67). These lamellipodia are sufficient to encapsulate nanoporous sensors, but not large devices in the absence of inflammatory cells, such as monocytes. About 12 hours after implantation, the activated microglia begin effecting whole-body movements towards the site of implantation, and can surround the implant with a thin cellular sheath by 24 hours. In addition, during the first week of implantation, astrocytes are fully activated, migrate to the site of implantation and, by the second to the third week, form a dense layer around the activated microglia (Kozai, et al., ACS Chem. Neurosci. 2015, 6, 48-67). Further, disruption of the blood-brain barrier leads to the secretion of pro-inflammatory molecules that non-specifically adsorb onto the surface of the implants, and propagate acute tissue inflammation to a chronic tissue response (Leung, et al., Biomaterials 2008, 29, 3289-3297). The final pathological product of this response is the walling off of the implant from the surrounding host tissue, and as well as altering the microenvironment of the surrounding tissue. A growing body of evidence shows that the foreign body response to neurological implants can also influence the electrophysiology and neurobiology of surrounding neurons and neural circuitry by a variety of confounding mechanisms unique to the tissue composition of the CNS (Skousen, et al., Biomaterials 2015, 36, 33-43). These adverse outcomes limit the clinical usefulness of neurological implants, and emphasize the critical need for neurological implants that have reduced and/or no insertion injury, foreign body responses, or both, in order to overcome this key challenge to both short and long-term function of neurological implants.

Approaches to improve the performance of neurological implants include inserting devices at away from major vascular structures, using neurological implants made from flexible and soft materials to reduce mechanical strain on tissue, reducing the size of the implant, increasing their surface permeability to act as sinks for pro-inflammatory cytokines, or using biomimetic and non-fouling coatings (Kozai, et al., ACS Chem. Neurosci. 2015, 6, 48-67; Skousen, et al., Biomaterials 2015, 36, 33-43). Despite all these efforts, neurological implants still possess problems in long-term applications, such as glial activation and failure of the non-fouling properties (Kozai, et al., ACS Chem. Neurosci. 2015, 6, 48-67; Prodanov and Delbeke, Front. Neurosci. 2016, 10(11), 1-20).

Therefore, the development of neurological implants that reduce and/or eliminate insertion injury, foreign body responses, for protracted periods of time is important for improving the performance (e.g. accuracy, reliability, and longevity) and safety of such devices, and remains an unmet need. Accordingly, the search for neurological implants of clinical relevance that address these problems, i.e., ameliorate biocompatibility, remains an area of active research.

Therefore, it is an object of the invention to provide neurological implants with improved beneficial effects.

It is another object of the invention to provide neurological implants that show reduced insertion injury and/or resist host foreign body response for protracted periods of time.

It is also an object of the invention to provide chemically modified neurological implants that elicit a lower foreign body response for protracted periods of time, compared to a corresponding neurological implant that lacks the chemical modification.

It is also an object of the invention to provide chemically modified neurological implants that reduce the recruitment of astrocytes and microglia cells to a site of implantation for protracted periods of time, compared to a corresponding neurological implant that lacks the chemical modification.

SUMMARY OF THE INVENTION

Neurological implants containing a surface that is partially or completely coated with one or more layers of an anti-inflammatory small molecule or chemical moiety (collectively compound) have improved properties, e.g., reduced foreign body response (e.g. recruitment of microglia cells, astrocytes, or both), following implantation into a part of the CNS of a host, as compared to a corresponding neurological implant that lacks the small molecule or chemical moiety on its surface. The implant can be formed of, or coated with, on one or more surfaces, the anti-inflammatory molecules.

Preferably, the surface is covalently modified using the compounds (small molecules or chemical moieties) described herein after formation of the neurological implant. The small molecules or chemical moieties contain a substituted heteroaryl group that includes an aryl group, a heterocyclic group, or a combination thereof. Preferably, the aryl group is aniline. Preferably, the heterocyclic group is tetrahydropyran, or thiomorpholine-1,1-dioxide. Preferably, the chemical moiety is

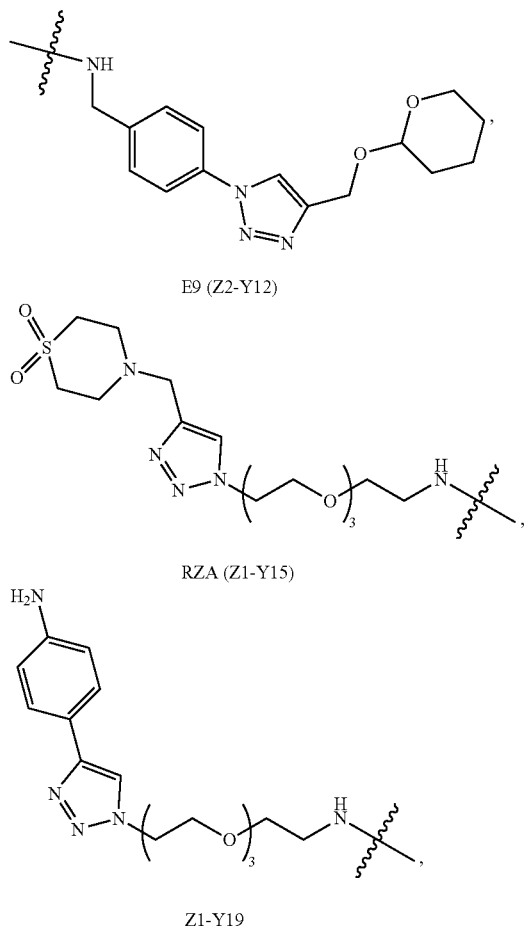

or combinations thereof.

In some forms, the surface of the neurological implant contains polydimethylsiloxane (PDMS). Preferably, the neurological implant is a clinical grade PDMS ventricular catheter.

Also described are methods of chemically modifying a surface of the neurological implants. The surface can be pre-treated plasma, to introduce functional groups such as hydroxyl, carboxyl, ester, aldehyde, ketone, and carbonate using oxygen plasma. In some forms, before or after treatment of the surface with plasma, the surface can be pretreated with an epoxy-silane (3-glycidoxypropyl-trimethoxy-silane) via chemical vapor deposition. Following pre-treatment, the small molecules react with the surface to introduce the chemical moieties described herein.

The implants are placed adjacent to or within neurological tissue, either within the central nervous system (CNS) or peripherally. The neurological implants can be used in acute and chronic applications including, but not limited to, draining fluids in patients with hydrocephalus.

BRIEF DESCRIPTION OF THE DRAWINGS

FIG. 1 is a graph of cell counts, obtained at 100-μm intervals from the catheter tract and normalized for cubic area are plotted with standard deviations presented as above/below error bars. Note that at distances beyond 1 cm ($10^{th}$ 100-μm interval) there is a significant difference between the immune response to the control catheter and the E9- and RZA15-coated catheters, with the RZA15-coated catheters in particular demonstrating reduced cell numbers reflective of an attenuated immune response.

DETAILED DESCRIPTION OF THE INVENTION

I. Definitions

"Biocompatible," as used herein, refers to a substance or object that performs its desired function when introduced into an organism without inducing significant inflammatory response, immunogenicity, or cytotoxicity to native cells, tissues, or organs. For example, a biocompatible product is a product that performs its desired function when introduced into an organism without inducing significant inflammatory response, immunogenicity, or cytotoxicity to native cells, tissues, or organs. Biocompatibility, as used herein, can be quantified using the in vivo biocompatibility assay described below.

In this assay, a material or product can be considered biocompatible if it produces, in a test of biocompatibility related to immune system reaction, less than 50%, 45%, 40%, 35%, 30%, 25%, 20%, 15%, 10%, 8%, 6%, 5%, 4%, 3%, 2%, or 1% of the reaction, in the same test of biocompatibility, produced by a material or product the same as the test material or product except for a lack of the surface modification on the test material or product. Examples of useful biocompatibility tests include measuring and assessing cytotoxicity in cell culture, inflammatory response after implantation (such as by fluorescence detection of cathepsin activity), and immune system cells recruited to implant (for example, macrophages and neutrophils).

"Foreign body response" as used herein, refers to the immunological response of biological tissue to the presence of any foreign material in the tissue which can include protein adsorption, macrophages, multinucleated foreign body giant cells, fibroblasts, and angiogenesis.

"Coating" as used herein, refers to any temporary, semi-permanent or permanent layer, covering or surface. A coating can be applied as a gas, vapor, liquid, paste, semi-solid, or solid. In addition, a coating can be applied as a liquid and solidified into a hard coating. Elasticity can be engineered into coatings to accommodate pliability, e.g. swelling or shrinkage, of the substrate or surface to be coated.

"Chemical modification" and related terms, as used herein in the context of the products, refers to chemical modification of the product. "Product" can include devices, such as the neurological implants described herein. Generally, such chemical modification is by direct attachment, coupling, or adherence of a compound to the surface material of the product. Preferably, the chemical modification involves modification with one or more of the compounds. Chemical modification, as defined herein in the context of the products, can be accomplished at any time and in any manner, including, for example, synthesis or production of the modified form of the product or material when the product or material is formed, addition of the chemical modification after the final product or material is formed, or at any time in between. The terms "replaced," "replace," "modified," "singularly modified," "singular modification," "multiply modified," "multiple modifications", "chemically modified," "surface modified," "modification," "chemical modification," "surface modification," "substituted," "substitution," "derived from," "based on," or "derivatized," and similar terms, as used herein to describe a structure, do not limit the structure to one made from a specific starting material or by a particular synthetic route. Except where specifically and expressly provided to the contrary, the terms refer to a structural property, regardless of how the structure was formed, and the structure is not limited to a structure made by any specific method.

In some embodiments, where explicitly indicated, addition or application of a material, compound, or composition to a starting material or intermediate before it is made into or incorporated into the final product can be specifically excluded. Thus, for example, chemical modification of alginate or another polymer prior to the polymer being incorporated into a capsule or other structure can be, in some embodiments, specifically excluded as the manner of producing a chemical modification of the capsule or structure. As another example, coating a device, prosthesis, or other product with a material that is chemically modified prior to being applied as a coating can be, in some embodiments, specifically excluded as the manner of producing a chemical modification of the device, prosthesis, or product. However, for such embodiments where such specific exclusions are used, so long as the product was itself chemically modified, coating of or addition to the product of another material that has chemical modifications does not alter the fact that the product was chemically modified according to the meaning of the term used herein.

"Surface modification" and related terms, as used herein in the context of a product, e.g., the products, refers to chemical modification of the surface or a surface of the product. Generally, such surface modification is by direct attachment, coupling, or adherence of a compound to the surface material of the product. Preferably, the surface modification involves modification with one or more of the compounds. Surface modification, as defined herein in the context of the products, can be accomplished at any time and in any manner, including, for example, synthesis or production of the modified form of the product or material when the product or material is formed, addition of the chemical modification after the final product or material is formed, or at any time in between. Except where specifically and expressly provided to the contrary, the term "surface modification" refers to a structural property, regardless of how the structure was formed, and the structure is not limited to a structure made by any specific method.

In some embodiments, where explicitly indicated, addition or application of a material, compound, or composition to a starting material or intermediate before it is made into or incorporated into the final product can be specifically excluded. Thus, for example, chemical or surface modification of alginate or another polymer prior to the polymer being incorporated into a capsule or other structure can be, in some embodiments, specifically excluded as the manner of producing a surface modification of the capsule or structure. As another example, coating a device, prosthesis, or other product with a material that was chemically modified prior to being applied as a coating can be, in some embodiments, specifically excluded as the manner of producing a surface modification of the device, prosthesis, or product. However, for such embodiments where such specific exclusions are used, so long as the product was itself surface modified, coating of or addition to the product of another material that has chemical modifications does not alter the fact that the product was surface modified according to the meaning of the term used herein.

In some embodiments, the moieties or compounds modifying the product can be present on the surface or a surface of the product, and are not present, or are not present in a significant amount, elsewhere in the product, e.g., on internal or interior surfaces. In some embodiments, at least 50, 60, 70, 80, 90, 95, or 99% of the moieties or compounds are present on the surface or a surface of the product. In some embodiments, the moieties or compounds are present on the exterior face of the surface or a surface of the product, and are not present, or not present in a significant amount, elsewhere in the product, e.g., on internal or interior surfaces. In some embodiments, at least 50, 60, 70, 80, 90, 95, or 99% of the moieties or compounds are present on the external face of the surface or a surface of the product.

In some embodiments, the moieties or compounds modifying the product can be present on a portion or component of the product, and are not present, or are not present in a significant amount, elsewhere in the product. In some embodiments, at least 50, 60, 70, 80, 90, 95, or 99% of the moieties or compounds are present on the portion or component of the product. In some embodiments, the moieties or compounds are present on the exterior face of the portion or component of the product, and are not present, or not present in a significant amount, elsewhere in the product. In some embodiments, at least 50, 60, 70, 80, 90, 95, or 99% of the moieties or compounds are present on the external face of the portion or component of the product.

"Surface," as used herein in the context of the products, refers to the exterior or outer boundary of a product. Generally, the surface or a surface of a product corresponds to the idealized surface of a three dimensional solid that is topological homeomorphic with the product. The surface or a surface of the product can be an exterior surface or an interior surface of the product. An exterior surface forms the outermost layer of a product or device. An interior surface surrounds an inner cavity of a product or device, such as the inner cavity of a tube. As an example, both the outside surface of a tube and the inside surface of a tube are part of the surface or a surface of the tube. However, internal surfaces of the product that are not in topological communication with the exterior surface, such as a tube with closed ends, can be excluded as the surface or a surface of a product. Preferred surfaces to be chemically modified are the outside surface and surfaces that can contact immune system components. Where the product is porous or has holes in its mean (idealized or surface, the internal faces of passages and holes would not be considered part of the surface or a surface of the product if its opening on the mean surface of the product is less than 5 nm.

"Implanting," as used herein, refers to the insertion or grafting into the body of a subject a product or material.

The phrase "effective amount," as used herein in the context of a coating, generally refers to the amount of the coating applied to the implant in order to provide one or more clinically measurable endpoints, such as reduced foreign body response compared to an uncoated implant, an implant coated with an unmodified coating, or another suitable control. The phrase "effective amount," as used herein in the context of a cell, capsule, product, device, material, composition, or compound, refers to a nontoxic but sufficient amount of the cell, capsule, product, device, material, composition, or compound to provide the desired result. The exact amount required may vary from subject to subject, depending on the species, age, and general condition of the subject; the severity of the disease that is being treated; the particular cell, capsule, product, device, material, composition, or compound used; its mode of administration; and other routine variables. An appropriate effective amount can be determined by one of ordinary skill in the art using only routine experimentation.

The terms "inhibit" and "reduce" means to reduce or decrease in activity or expression. This can be a complete inhibition or reduction of activity or expression, or a partial inhibition or reduction. Inhibition or reduction can be compared to a control or to a standard level. Inhibition can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

"Small molecule" generally refers to an organic molecule that is less than about 2000 g/mol in molecular weight, less than about 1500 g/mol, less than about 1000 g/mol, less than about 800 g/mol, or less than about 500 g/mol. In some forms, small molecules are non-polymeric and/or non-oligomeric.

"Substituted," as used herein, refers to all permissible substituents of the compounds or functional groups described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, arylalkyl, substituted arylalkyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups.

Such alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, arylalkyl, substituted arylalkyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups can be further substituted.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

Except where specifically and expressly provided to the contrary, the term "substituted" refers to a structure, e.g., a chemical compound or a moiety on a larger chemical compound, regardless of how the structure was formed. The structure is not limited to a structure made by any specific method.

"Aryl," as used herein, refers to $C_5$-$C_{26}$-membered aromatic, fused aromatic, fused heterocyclic, or biaromatic ring systems. Broadly defined, "aryl," as used herein, includes 5-, 6-, 7-, 8-, 9-, 10-, 14-, 18-, and 24-membered single-ring aromatic groups, for example, benzene, naphthalene, anthracene, phenanthrene, chrysene, pyrene, corannulene, coronene, etc.

"Aryl" further encompasses polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles.

The term "substituted aryl" refers to an aryl group, wherein one or more hydrogen atoms on one or more aromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfoxide, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

"Heterocycle," "heterocyclic" and "heterocyclyl" are used interchangeably, and refer to a cyclic radical attached via a ring carbon or nitrogen atom of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, $C_1$-$C_{10}$ alkyl, phenyl or benzyl, and optionally containing 1-3 double bonds and optionally substituted with one or more substituents. Heterocyclyl are distinguished from heteroaryl by definition. Examples of heterocycles include, but are not limited to piperazinyl, piperidinyl, piperidonyl, 4-piperidonyl, dihydrofuro[2,3-b]tetrahydrofuran, morpholinyl, piperazinyl, piperidinyl, piperidonyl, 4-piperidonyl, piperonyl, pyranyl, 2H-pyrrolyl, 4H-quinolizinyl, quinuclidinyl, tetrahydrofuranyl, 6H-1,2,5-thiadiazinyl. Heterocyclic groups can optionally be substituted with one or more substituents as defined above for alkyl and aryl.

The term "heteroaryl" refers to $C_5$-$C_{26}$-membered aromatic, fused aromatic, biaromatic ring systems, or combinations thereof, in which one or more carbon atoms on one or more aromatic ring structures have been substituted with a heteroatom. Suitable heteroatoms include, but are not limited to, oxygen, sulfur, and nitrogen. Broadly defined, "heteroaryl," as used herein, includes 5-, 6-, 7-, 8-, 9-, 10-, 14-, 18-, and 24-membered single-ring aromatic groups that may include from one to four heteroatoms, for example, pyrrole, furan, thiophene, imidazole, oxazole, thiazole, triazole, tetrazole, pyrazole, pyridine, pyrazine, pyridazine and pyrimidine, and the like. The heteroaryl group may also be referred to as "aryl heterocycles" or "heteroaromatics". "Heteroaryl" further encompasses polycyclic ring systems having two or more rings in which two or more carbons are common to two adjoining rings (i.e., "fused rings") wherein at least one of the rings is heteroaromatic, e.g., the other cyclic ring or rings can be cycloalkyls, cycloalkenyls, cycloalkynyls, aryls, heterocycles, or combinations thereof. Examples of heteroaryl rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, purinyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, quinoxalinyl, tetrahydroisoquinolinyl, tetrahydroquinolinyl, tetrazolyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined below for "substituted heteroaryl".

The term "substituted heteroaryl" refers to a heteroaryl group in which one or more hydrogen atoms on one or more heteroaromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quaternized amino), amido, amidine, imine, cyano, nitro, azido, sulfhydryl, imino, alkylthio, sulfate, sulfonate, sulfamoyl, sulfoxide, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

"Alkyl," as used herein, refers to the radical of saturated aliphatic groups, including straight-chain alkyl, alkenyl, or alkynyl groups, branched-chain alkyl, cycloalkyl (alicyclic), alkyl substituted cycloalkyl groups, and cycloalkyl substituted alkyl. In preferred embodiments, a straight chain or branched chain alkyl has 30 or fewer carbon atoms in its backbone (e.g., $C_1$-$C_{30}$ for straight chains, $C_3$-$C_{30}$ for branched chains), preferably 20 or fewer, more preferably 15 or fewer, most preferably 10 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a hosphinate, amino, amido, amidine, imine, cyano, nitro, azido, sulfhydryl, alkylthio, sulfate, sulfonate, sulfamoyl, sulfoxide, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

"Alkyl" includes one or more substitutions at one or more carbon atoms of the hydrocarbon radical as well as heteroalkyls. Suitable substituents include, but are not limited to, halogens, such as fluorine, chlorine, bromine, or iodine; hydroxyl; —NRR', wherein R and R' are independently hydrogen, alkyl, or aryl, and wherein the nitrogen atom is optionally quaternized; —SR, wherein R is hydrogen, alkyl, or aryl; —CN; —$NO_2$; —COOH; carboxylate; —COR, —COOR, or —CON(R)$_2$, wherein R is hydrogen, alkyl, or aryl; azide, aralkyl, alkoxyl, imino, phosphonate, phosphinate, silyl, ether, sulfonyl, sulfonamido, heterocyclyl, aromatic or heteroaromatic moieties, haloalkyl (such as —$CF_3$, —$CH_2$—$CF_3$, —$CCl_3$); —CN; —$NCOCOCH_2CH_2$, —NCOCOCHCH; —NCS; and combinations thereof.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl, sulfoxide, and sulfonate), and silyl groups, as well as ethers, alkylthios, carbonyls (including ketones, aldehydes, carboxylates, and esters), haloalkyls, —CN and the like. Cycloalkyls can be substituted in the same manner.

The terms "alkenyl" and "alkynyl" refer to unsaturated aliphatic groups analogous in length and possible substitution to the alkyls described above, but that contain at least one double or triple bond, respectively.

The term "substituted alkenyl" refers to alkenyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quaternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "substituted alkynyl" refers to alkynyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "phenyl" is art recognized, and refers to the aromatic moiety —$C_6H_5$, i.e., a benzene ring without one hydrogen atom.

The term "substituted phenyl" refers to a phenyl group, as defined above, having one or more substituents replacing one or more hydrogen atoms on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

"Amino" and "Amine," as used herein, are art-recognized and refer to both substituted and unsubstituted amines, e.g., a moiety that can be represented by the general formula:

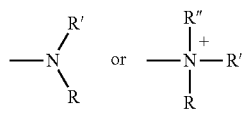

wherein, R, R', and R" each independently represent a hydrogen, substituted or unsubstituted alkyl, substituted or unsubstituted alkenyl, substituted or unsubstituted alkynyl, substituted or unsubstituted carbonyl, —$(CH_2)_m$—R'", or R and R' taken together with the N atom to which they are attached complete a heterocycle having from 3 to 14 atoms in the ring structure; R'" represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide. In preferred embodiments, R and R' (and optionally R") each independently represent a hydrogen atom, substituted or unsubstituted alkyl, a substituted or unsubstituted alkenyl, or —$(CH_2)_m$—R'". Thus, the term 'alkylamine' as used herein refers to an amine group, as defined above, having a substituted or unsubstituted alkyl attached thereto (i.e. at least one of R, R', or R" is an alkyl group).

"Carbonyl," as used herein, is art-recognized and includes such moieties as can be represented by the general formula:

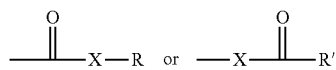

wherein X is a bond, or represents an oxygen or a sulfur, and R represents a hydrogen, a substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —$(CH_2)_m$—R", or a pharmaceutical acceptable salt, R' represents a hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl or —$(CH_2)_m$—R"; R" represents a hydroxy group, substituted or unsubstituted carbonyl group, an aryl, a cycloalkyl ring, a cycloalkenyl ring, a heterocycle, or a polycycle; and m is zero or an integer ranging from 1 to 8. Where X is oxygen and R is defines as above, the moiety is also referred to as a carboxyl group. When X is oxygen and R is hydrogen, the formula represents a 'carboxylic acid'. Where X is oxygen and R' is hydrogen, the formula represents a 'formate'. Where X is oxygen and R or R' is not hydrogen, the formula represents an "ester". In general, where the oxygen atom of the above formula is replaced by a sulfur atom, the formula represents a 'thiocarbonyl' group. Where X is sulfur and R or R' is not hydrogen, the formula represents a 'thioester.' Where X is sulfur and R is hydrogen, the formula represents a 'thiocarboxylic acid.' Where X is sulfur and R' is hydrogen, the formula represents a 'thioformate.' Where X is a bond and R is not hydrogen, the above formula represents a 'ketone.' Where X is a bond and R is hydrogen, the above formula represents an 'aldehyde.'

The term "substituted carbonyl" refers to a carbonyl, as defined above, wherein one or more hydrogen atoms in R, R' or a group to which the moiety

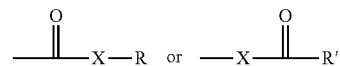

is attached, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "carboxyl" is as defined above for the formula

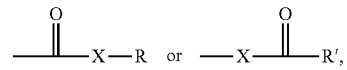

and is defined more specifically by the formula —$R^{iv}$COOH, wherein $R^{iv}$ is an alkyl, alkenyl, alkynyl, cycloalkyl, heterocyclyl, alkylaryl, arylalkyl, aryl, or heteroaryl. In preferred embodiments, a straight chain or branched chain alkyl, alkenyl, and alkynyl have 30 or fewer carbon atoms in its backbone (e.g., $C_1$-$C_{30}$ for straight chain alkyl, $C_3$-$C_{30}$ for branched chain alkyl, $C_2$-$C_{30}$ for straight chain alkenyl and alkynyl, $C_3$-$C_{30}$ for branched chain alkenyl and alkynyl), preferably 20 or fewer, more preferably 15 or fewer, most preferably 10 or fewer. Likewise, preferred cycloalkyls, heterocyclyls, aryls and heteroaryls have from 3-10 carbon atoms in their ring structure, and more preferably have 5, 6 or 7 carbons in the ring structure.

The term "substituted carboxyl" refers to a carboxyl, as defined above, wherein one or more hydrogen atoms in $R^{iv}$ are substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

"Heteroalkyl," as used herein, refers to straight or branched chain, or cyclic carbon-containing radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized.

Examples of saturated hydrocarbon radicals include, but are not limited to, methyl, ethyl, n-propyl, isopropyl, n-butyl, t-butyl, isobutyl, sec-butyl, cyclohexyl, (cyclohexyl)methyl, cyclopropylmethyl, and homologs and isomers of, for example, n-pentyl, n-hexyl, n-heptyl, n-octyl. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, and 3-butynyl.

The terms "alkoxyl" or "alkoxy," "aroxy" or "aryloxy," generally describe compounds represented by the formula —$OR^v$, wherein $R^v$ includes, but is not limited to, substituted or unsubstituted alkyl, alkenyl, alkynyl, cycloalkyl, heterocyclyl, cycloalkenyl, heterocycloalkenyl, aryl, heteroaryl, arylalkyl, heteroalkyls, alkylaryl, alkylheteroaryl.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. The term alkoxy also includes cycloalkyl, heterocyclyl, cycloalkenyl, heterocycloalkenyl, and arylalkyl having an oxygen radical attached to at least one of the carbon atoms, as valency permits.

The term "substituted alkoxy" refers to an alkoxy group having one or more substituents replacing one or more hydrogen atoms on one or more carbons of the alkoxy backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "phenoxy" is art recognized, and refers to a compound of the formula —$OR^v$ wherein $R^v$ is (i.e., —O—$C_6H_5$). One of skill in the art recognizes that a phenoxy is a species of the aroxy genus.

The term "substituted phenoxy" refers to a phenoxy group, as defined above, having one or more substituents replacing one or more hydrogen atoms on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The terms "aroxy" and "aryloxy," as used interchangeably herein, are represented by —O-aryl or —O-heteroaryl, wherein aryl and heteroaryl are as defined herein.

The terms "substituted aroxy" and "substituted aryloxy," as used interchangeably herein, represent —O-aryl or —O-heteroaryl, having one or more substituents replacing one or more hydrogen atoms on one or more ring atoms of the aryl and heteroaryl, as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "alkylthio" refers to an alkyl group, as defined above, having a sulfur radical attached thereto. The "alkylthio" moiety is represented by —S-alkyl. Representative alkylthio groups include methylthio, ethylthio, and the like. The term "alkylthio" also encompasses cycloalkyl groups having a sulfur radical attached thereto.

The term "substituted alkylthio" refers to an alkylthio group having one or more substituents replacing one or more hydrogen atoms on one or more carbon atoms of the alkylthio backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "phenylthio" is art recognized, and refers to —S—$C_6H_5$, i.e., a phenyl group attached to a sulfur atom.

The term "substituted phenylthio" refers to a phenylthio group, as defined above, having one or more substituents replacing a hydrogen on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

"Arylthio" refers to —S-aryl or —S-heteroaryl groups, wherein aryl and heteroaryl as defined herein.

The term "substituted arylthio" represents —S-aryl or —S-heteroaryl, having one or more substituents replacing a hydrogen atom on one or more ring atoms of the aryl and heteroaryl rings as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

"Arylalkyl," as used herein, refers to an alkyl group that is substituted with a substituted or unsubstituted aryl or heteroaryl group.

"Alkylaryl," as used herein, refers to an aryl group (e.g., an aromatic or hetero aromatic group), substituted with a substituted or unsubstituted alkyl group.

The terms "amide" or "amido" are used interchangeably, refer to both "unsubstituted amido" and "substituted amido" and are represented by the general formula:

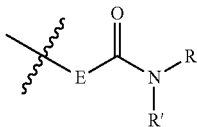

wherein, E is absent, or E is substituted or unsubstituted alkyl, substituted or unsubstituted alkenyl, substituted or unsubstituted alkynyl, substituted or unsubstituted aralkyl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide. In preferred embodiments, R and R' each independently represent a hydrogen atom, substituted or unsubstituted alkyl, a substituted or unsubstituted alkenyl, or —(CH$_2$)$_m$—R'''. When E is oxygen, a carbamate is formed. The carbamate cannot be attached to another chemical species, such as to form an oxygen-oxygen bond, or other unstable bonds, as understood by one of ordinary skill in the art.

The term "sulfonyl" is represented by the formula

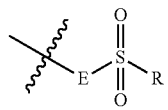

wherein E is absent, or E is alkyl, alkenyl, alkynyl, aralkyl, alkylaryl, cycloalkyl, aryl, heteroaryl, heterocyclyl, wherein independently of E, R represents a hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', or E and R taken together with the S atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of E and R can be substituted or unsubstituted amine, to form a "sulfonamide" or "sulfonamido." The substituted or unsubstituted amine is as defined above.

The term "substituted sulfonyl" represents a sulfonyl in which E, R, or both, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "sulfonic acid" refers to a sulfonyl, as defined above, wherein R is hydroxyl, and E is absent, or E is substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl.

The term "sulfate" refers to a sulfonyl, as defined above, wherein E is absent, oxygen, alkoxy, aroxy, substituted alkoxy or substituted aroxy, as defined above, and R is independently hydroxyl, alkoxy, aroxy, substituted alkoxy or substituted aroxy, as defined above. When E is oxygen, the sulfate cannot be attached to another chemical species, such as to form an oxygen-oxygen bond, or other unstable bonds, as understood by one of ordinary skill in the art.

The term "sulfonate" refers to a sulfonyl, as defined above, wherein E is oxygen, alkoxy, aroxy, substituted alkoxy or substituted aroxy, as defined above, and R is independently hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. When E is oxygen, sulfonate cannot be attached to another chemical species, such as to form an oxygen-oxygen bond, or other unstable bonds, as understood by one of ordinary skill in the art.

The term "sulfamoyl" refers to a sulfonamide or sulfonamide represented by the formula

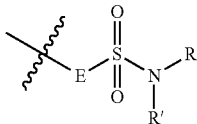

wherein E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide.

The term "sulfoxide" is represented by the formula

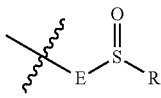

wherein E is absent, or E is alkyl, alkenyl, alkynyl, aralkyl, alkylaryl, cycloalkyl, aryl, heteroaryl, heterocyclyl, wherein independently of E, R represents a hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', or E and R taken together with the S atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8.

The term "phosphonyl" is represented by the formula

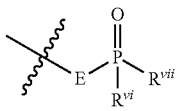

wherein E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein, independently of E, R$^{vi}$ and R$^{vii}$ are independently hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', or R and R' taken together with the P atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8.

The term "substituted phosphonyl" represents a phosphonyl in which E, R$^{vi}$ and R$^{vii}$ are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "phosphoryl" defines a phosphonyl in which E is absent, oxygen, alkoxy, aroxy, substituted alkoxy or substituted aroxy, as defined above, and independently of E, R$^{vi}$ and R$^{vii}$ are independently hydroxyl, alkoxy, aroxy, substituted alkoxy or substituted aroxy, as defined above. When E is oxygen, the phosphoryl cannot be attached to another chemical species, such as to form an oxygen-oxygen bond, or other unstable bonds, as understood by one of ordinary skill in the art. When E, R$^{vi}$ and R$^{vii}$ are substituted, the substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "polyaryl" refers to a chemical moiety that includes two or more aryls, heteroaryls, and combinations thereof. The aryls, heteroaryls, and combinations thereof, are fused, or linked via a single bond, ether, ester, carbonyl, amide, sulfonyl, sulfonamide, alkyl, azo, and combinations thereof.

The term "substituted polyaryl" refers to a polyaryl in which one or more of the aryls, heteroaryls are substituted, with one or more substituents including, but not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "$C_3$-$C_{20}$ cyclic" refers to a substituted or unsubstituted cycloalkyl, substituted or unsubstituted cycloalkenyl, substituted or unsubstituted cycloalkynyl, substituted or unsubstituted heterocyclyl that have from three to 20 carbon atoms, as geometric constraints permit. The cyclic structures are formed from single or fused ring systems. The substituted cycloalkyls, cycloalkenyls, cycloalkynyls and heterocyclyls are substituted as defined above for the alkyls, alkenyls, alkynyls and heterocyclyls, respectively.

The terms "hydroxyl" and "hydroxy" are used interchangeably and are represented by —OH.

The terms "thiol" and "sulfhydryl" are used interchangeably and are represented by —SH.

The term "oxo" refers to =O bonded to a carbon atom.

The terms "cyano" and "nitrile" are used interchangeably to refer to —CN.

The term "nitro" refers to —$NO_2$.

The term "phosphate" refers to —O—$PO_3$.

The term "azide" or "azido" are used interchangeably to refer to —$N_3$.

The term "substituted $C_1$-$C_x$ alkyl" refers to alkyl groups having from one to x carbon atoms, wherein at least one carbon atom is substituted, wherein "x" is an integer from one to ten. The term "unsubstituted $C_1$-$C_x$ alkyl" refers to alkyl groups having from one to x carbon atoms that are not substituted, wherein "x" is an integer from one to ten.

The term "substituted $C_1$-$C_x$ alkylene" refers to alkylene groups having from one to x carbon atoms, wherein at least one carbon atom is substituted, wherein "x" is an integer from one to ten. The term "unsubstituted $C_1$-$C_x$ alkylene" refers to alkylene groups having from one to x carbon atoms that are not substituted, wherein "x" is an integer from one to ten. The term "alkylene" as used herein, refers to a moiety with the formula —$(CH_2)_a$—, wherein "a" is an integer from one to ten.

The term "substituted $C_2$-$C_x$ alkenyl" refers to alkenyl groups having from two to x carbon atoms, wherein at least one carbon atom is substituted, wherein "x" is an integer from two to ten. The term "unsubstituted $C_2$-$C_x$ alkenyl" refers to alkenyl groups having from two to x carbon atoms that are not substituted, wherein "x" is an integer from two to ten.

The term "substituted $C_2$-$C_x$ alkynyl" refers to alkynyl groups having from two to x carbon atoms, wherein at least one carbon atom is substituted, wherein "x" is an integer from two to ten. The term "unsubstituted $C_2$-$C_x$ alkynyl" refers to alkynyl groups having from two to x carbon atoms that are not substituted, wherein "x" is an integer from two to ten.

The term "substituted $C_1$-$C_x$ alkoxy" refers to alkoxy groups having from one to x carbon atoms, wherein at least one carbon atom is substituted, wherein "x" is an integer from one to ten. The term "unsubstituted $C_1$-$C_x$ alkoxy" refers to alkoxy groups having from one to x carbon atoms that are not substituted, wherein "x" is an integer from one to ten.

The term "substituted $C_1$-$C_x$ alkylamino" refers to alkylamino groups having from one to x carbon atoms, wherein at least one carbon atom is substituted, wherein "x" is an integer from one to ten. The term "unsubstituted $C_1$-$C_x$ alkylamino" refers to alkyl groups having from one to x carbon atoms that are not substituted, wherein "x" is an integer from one to ten. The terms "alkylamine" and "alkylamino" are used interchangeably. In any alkylamino, where the nitrogen atom is substituted with one, two, or three substituents, the nitrogen atom can be referred to as a secondary, tertiary, or quarternary nitrogen atom, respectively.

The term "substituted $C_1$-$C_x$ alkylthio" refers to alkylthio groups having from one to x carbon atoms, wherein at least one carbon atom is substituted, wherein "x" is an integer from one to ten. The term "unsubstituted $C_1$-$C_x$ alkylthio" refers to alkylthio groups having from one to x carbon atoms that are not substituted, wherein "x" is an integer from one to ten.

The term "substituted $C_1$-$C_x$ carbonyl" refers to carbonyl groups having from one to x carbon atoms, wherein at least one carbon atom is substituted, wherein "x" is an integer from one to ten. The term "unsubstituted $C_1$-$C_x$ carbonyl" refers to carbonyl groups having from one to x carbon atoms that are not substituted, wherein "x" is an integer from one to ten.

The term "substituted $C_1$-$C_x$ carboxyl" refers to carboxyl groups having from one to x carbon atoms, wherein at least one carbon atom is substituted, wherein "x" is an integer from one to ten. The term "unsubstituted $C_1$-$C_x$ carboxyl" refers to carboxyl groups having from one to x carbon atoms that are not substituted, wherein "x" is an integer from one to ten.

The term "substituted $C_1$-$C_x$ amido" refers to amido groups having from one to x carbon atoms, wherein at least one carbon atom is substituted, wherein "x" is an integer from one to ten. The term "unsubstituted $C_1$-$C_x$ amido" refers to amido groups having from one to x carbon atoms that are not substituted, wherein "x" is an integer from one to ten.

The term "substituted $C_1$-$C_x$ sulfonyl" refers to sulfonyl groups having from one to x carbon atoms, wherein at least one carbon atom is substituted, wherein "x" is an integer from one to ten. The term "unsubstituted $C_1$-$C_x$ sulfonyl" refers to sulfonyl groups having from one to x carbon atoms that are not substituted, wherein "x" is an integer from one to ten.

The term "substituted $C_1$-$C_x$ sulfonic acid" refers to sulfonic acid groups having from one to x carbon atoms, wherein at least one carbon atom is substituted, wherein "x" is an integer from one to ten. The term "unsubstituted $C_1$-$C_x$ sulfonic acid" refers to sulfonic acid groups having from one to x carbon atoms that are not substituted, wherein "x" is an integer from one to ten.

The term "substituted $C_1$-$C_x$ sulfamoyl" refers to sulfamoyl groups having from one to x carbon atoms, wherein at least one carbon atom is substituted, wherein "x" is an integer from one to ten. The term "unsubstituted $C_1$-$C_x$ sulfamoyl" refers to sulfamoyl groups having from one to x carbon atoms that are not substituted, wherein "x" is an integer from one to ten.

The term "substituted $C_1$-$C_x$ sulfoxide" refers to sulfoxide groups having from one to x carbon atoms, wherein at least one carbon atom is substituted, wherein "x" is an integer from one to ten. The term "unsubstituted $C_1$-$C_x$ sulfoxide" refers to sulfoxide groups having from one to x carbon atoms that are not substituted, wherein "x" is an integer from one to ten.

The term "substituted $C_1$-$C_x$ phosphoryl" refers to phosphoryl groups having from one to x carbon atoms, wherein at least one carbon atom is substituted, wherein "x" is an integer from one to ten. The term "unsubstituted $C_1$-$C_x$ phosphoryl" refers to phosphoryl groups having from one to x carbon atoms that are not substituted, wherein "x" is an integer from one to ten.

The term "substituted $C_1$-$C_x$ phosphonyl" refers to phosphonyl groups having from one to x carbon atoms, wherein at least one carbon atom is substituted, wherein "x" is an integer from one to ten. The term "unsubstituted $C_1$-$C_x$ phosphonyl" refers to phosphonyl groups having from one to x carbon atoms that are not substituted, wherein "x" is an integer from one to ten.

The term "substituted $C_0$-$C_x$ sulfonyl" refers to sulfonyl groups having from zero to x carbon atoms, wherein, if present, at least one carbon atom is substituted, wherein "x" is an integer from zero to ten. The term "unsubstituted $C_0$-$C_x$ sulfonyl" refers to sulfonyl groups having from zero to x carbon atoms that are not substituted, wherein "x" is an integer from zero to ten.

The term "substituted $C_0$-$C_x$ sulfonic acid" refers to sulfonic acid groups having from zero to x carbon atoms, wherein, if present, at least one carbon atom is substituted, wherein "x" is an integer from zero to ten. The term "unsubstituted $C_0$-$C_x$ sulfonic acid" refers to sulfonic acid groups having from zero to x carbon atoms that are not substituted, wherein "x" is an integer from zero to ten.

The term "substituted $C_0$-$C_x$ sulfamoyl" refers to sulfamoyl groups having from zero to x carbon atoms, wherein, if present, at least one carbon atom is substituted, wherein "x" is an integer from zero to ten. The term "unsubstituted $C_0$-$C_x$ sulfamoyl" refers to sulfamoyl groups having from zero to x carbon atoms that are not substituted, wherein "x" is an integer from zero to ten.

The term "substituted $C_0$-$C_x$ sulfoxide" refers to sulfoxide groups having from zero to x carbon atoms, wherein at least one carbon atom is substituted, wherein "x" is an integer from zero to ten. The term "unsubstituted $C_0$-$C_x$ sulfoxide" refers to sulfoxide groups having from zero to x carbon atoms that are not substituted, wherein "x" is an integer from zero to ten.

The term "substituted $C_0$-$C_x$ phosphoryl" refers to phosphoryl groups having from zero to x carbon atoms, wherein, if present, at least one carbon atom is substituted, wherein "x" is an integer from zero to ten. The term "unsubstituted $C_0$-$C_x$ phosphoryl" refers to phosphoryl groups having from zero to x carbon atoms that are not substituted, wherein "x" is an integer from zero to ten.

The term "substituted $C_0$-$C_x$ phosphonyl" refers to phosphonyl groups having from zero to x carbon atoms, wherein, if present, at least one carbon atom is substituted, wherein "x" is an integer from zero to ten. The term "unsubstituted $C_0$-$C_x$ phosphonyl" refers to phosphonyl groups having from zero to x carbon atoms that are not substituted, wherein "x" is an integer from zero to ten.

The terms substituted "$C_x$ alkyl," "$C_x$ alkylene," "$C_x$ alkenyl," "$C_x$ alkynyl," "$C_x$ alkoxy," "$C_x$ alkylamino," "$C_x$ alkylthio," "$C_x$ carbonyl," "$C_x$ carboxyl," "$C_x$ amido," "$C_x$ sulfonyl," "$C_x$ sulfonic acid," "$C_x$ sulfamoyl," "$C_x$ phosphoryl," and "$C_x$ phosphonyl" refer to alkyl, alkylene, alkenyl, alkynyl, alkoxy, alkylamino, alkylthio, carbonyl, carboxyl, amido, sulfonyl, sulfonic acid, sulfamoyl, sulfoxide, phosphoryl, and phosphonyl groups, respectively, having x carbon atoms, wherein at least one carbon atom is substituted, wherein "x" is an integer from one to ten. The terms unsubstituted "$C_x$ alkyl," "$C_x$ alkylene," "$C_x$ alkenyl," "$C_x$ alkynyl," "$C_x$ alkoxy," "$C_x$ alkylamino", "$C_x$ alkylthio," "$C_x$ carbonyl," "$C_x$ carboxyl," "$C_x$ amido," "$C_x$ sulfonyl," "$C_x$ sulfonic acid," "$C_x$ sulfamoyl," "$C_x$ phosphoryl," and "$C_x$ phosphonyl" refer to alkyl, alkylene, alkenyl, alkynyl, alkoxy, alkylamino, alkylthio, carbonyl, carboxyl, amido, sulfonyl, sulfonic acid, sulfamoyl, sulfoxide, phosphoryl, and phosphonyl groups, respectively, having x carbon atoms that are not substituted, wherein "x" is an integer from one to ten.

The terms unsubstituted "$C_0$ sulfonyl," "$C_0$ sulfonic acid," "$C_0$ sulfamoyl," "$C_0$ phosphoryl," and "$C_0$ phosphonyl" refer to alkyl, alkylene, alkenyl, alkynyl, alkoxy, alkylamino, alkylthio, carbonyl, carboxyl, amido, sulfonyl, sulfonic acid, sulfamoyl, sulfoxide, phosphoryl, and phosphonyl groups, respectively, having zero carbon atoms that are not substituted.

II. Compositions

Neurological implants containing a surface that is partially or completely coated with one or more layers of a small molecule or chemical moiety derived from a small molecule have improved properties, including reduced foreign body response, following implantation into a part of the CNS of a host, as compared to a corresponding neurological implant that lacks the small molecule or chemical moiety on its surface. The neurological implants coated with a small molecules show reduced recruitment of microglia cells, astrocytes, or both, to the site of implantation, compared to a corresponding neurological implant lacking the small molecule or chemical moiety.

Preferably, the small molecule or chemical moiety contains a substituted heteroaryl group. In some forms, the substituted heteroaryl group contains an aryl group, a heterocyclic group, or a combination thereof. In some forms the aryl group can be aniline. In some forms, the heterocyclic group can be tetrahydropyran, or thiomorpholine-1,1-dioxide. In some forms, the substituted heteroaryl group is a substituted triazole, such as a 1,2,3-triazole. In some forms, the chemical moiety can be:

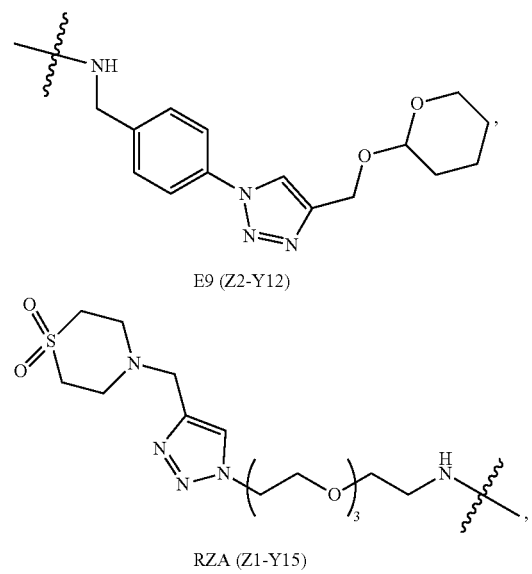

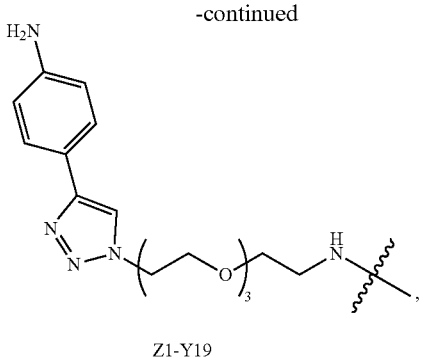

Z1-Y19 or combinations thereof.

In some forms, the density of the chemical moiety on the surface is between 1 and 10,000 modifications, inclusive, per square μm. In some forms, the one or more layers containing the chemical moieties have a thickness of between 10 nm and 1 mm, inclusive. In some forms, the chemical moiety forms a conformal coating on the surface. In some forms the chemical moiety is indirectly or directly attached covalently to the surface.

A. Neurological Implants

Neurological implants can include devices used to restore, replace, or bypass lost neurological functions due to diseases or injuries to parts of the CNS. Any neurological implant can be modified using the chemical modifications described herein. Preferably, a surface of the neurological implant is chemically modified after formation of the neurological implant with one or more compounds. Exemplary neurological implants include neurological shunts (e.g. ventricular catheters), cortical electrode arrays, neurological leads, microdialysis sampling probes, and carbon fiber/microwire-based microfabrication-based probes for amperometry, voltammetry, for electrophysiological recording.

Other types of devices include hearing and eye implants, brain implants, pumps, cardiac pacemaker leads, and other devices which conduct electrical impulses.

Other types of devices are those which are implanted in abutment with neurological tissues. An example is a titanium plate and screws used to repair a wrist bone immediately adjacent to the nerves which pass through into the hand. This may obviate or reduce the need for subsequent injection of anti-inflammatory into the region adjacent to the nerve. In these embodiments, the anti-inflammatory molecules are bound to a surface coating, which may be placed only on the surface adjacent to the nerve impacted by the implant.

B. Materials Forming Implants or Coatings Thereon

The devices may be formed of or coated with material to which the anti-inflammatory molecules are bound, as described in more detail below.

In the preferred embodiment, the anti-inflammatory is bound to a biocompatible polymer, which may be degradable or not degradable. This may be used to form the device, or to coat all or a portion of the device. Alternatively, the anti-inflammatory molecules can be bound to a material such as a ceramic or ceramic-hydroxyapatite mixture or metal such as titanium.

For example, the surface of a neurological implant may contain polydimethylsiloxane (PDMS). The surface of the neurological implant may be formed or coated with the PDMS. In some forms, the neurological implant is formed entirely of the polymer, such as a PDMS ventricular catheter, preferably of clinical grade.

The neurological implants possess physical properties that facilitate their insertion and passage into the CNS or peripheral nerve tissue. In some forms, the neurological implants also possess physical properties, such as flexibility and softness, which reduce mechanical strain exerted on surrounding tissue during and/or after implantation. In some forms, the neurological implants contain soft, pliable polymeric materials. Examples of soft pliable polymeric materials include, but are not limited to, polydimethylsiloxane (PDMS), soft thermoplastic polyolefins (e.g. polyethylene and polypropylene), polyurethanes, polyesters and other suitable thermoplastic polymers. Typically this polymeric material will have a Shore hardness between about A10 and about A60, inclusive, measured using a Rex durometer model 1000 A, on an appropriate sample size.

More examples of useful materials are described below under methods of manufacture.

C. Chemical Moieties Derived from Small Molecules

The neurological implant can be completely or partially coated with one or more layers containing a small molecule containing a chemical moiety having the formula:

Formula XII

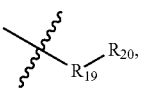

wherein $R_{19}$ and $R_{20}$ are independently unsubstituted alkyl, substituted alkyl, unsubstituted alkenyl, substituted alkenyl, unsubstituted alkynyl, substituted alkynyl, unsubstituted aryl, substituted aryl, unsubstituted heteroaryl, substituted heteroaryl, unsubstituted alkoxy, substituted alkoxy, unsubstituted aroxy, substituted aroxy, unsubstituted alkylthio, substituted alkylthio, unsubstituted arylthio, substituted arylthio, unsubstituted carbonyl, substituted carbonyl, unsubstituted carboxyl, substituted carboxyl, unsubstituted amino, substituted amino, unsubstituted amido, substituted amido, unsubstituted sulfonyl, substituted sulfonyl, unsubstituted sulfamoyl, substituted sulfamoyl, unsubstituted phosphonyl, substituted phosphonyl, —O—, —S—, —NH—NHC(O)—, —N=N—, —N=CH—, unsubstituted polyaryl, substituted polyaryl, unsubstituted $C_3$-$C_{20}$ cyclic, substituted $C_3$-$C_{20}$ cyclic, unsubstituted $C_3$-$C_{20}$ heterocyclic, substituted $C_3$-$C_{20}$ heterocyclic, amino acid, poly(ethylene glycol), poly(lactic-co-glycolic acid), peptide, or polypeptide group.

In some forms, $R_{19}$, $R_{20}$, or both contain a substituted heteroaryl group, such as a substituted 1,2,3-triazole.

In some forms, $R_{19}$ is —NRx-, —O—, —S—, —C(O)NH—, —C(O)O—, —NHC(O)—, —OC(O)—, —NH—NHC(O)—, —OC(O)NH—, —NHC(O)O—, —C(O)—, —OC(O)O—, —S(=O$_2$)$_2$—, —S(=O)—, —N=N—, or —N=CH—, wherein Rx is hydrogen, unsubstituted alkyl, substituted alkyl, unsubstituted alkenyl, substituted alkenyl, unsubstituted alkynyl, substituted alkynyl, unsubstituted aryl, substituted aryl, unsubstituted heteroaryl, or substituted heteroaryl, preferably, $R_{19}$ can be —NRx-, —O—, —S—, —C(O)NH—, —C(O)O—, —NHC(O)—, —OC(O)—, wherein Rx is hydrogen, unsubstituted alkyl, or substituted alkyl.

In some forms of Formula XII, $R_{20}$ has the structure:

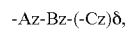

-Az-Bz-(-Cz)δ,  Formula XIII wherein δ is an integer between 0 and 10, inclusive, preferably δ is 1.

In some forms of Formula XIII, Az can be

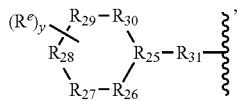

Formula XIV wherein in Formula XIV of Az: $R_{31}$—$(CR_{32}R_{32})_p$—; p is an integer from 0 to 5; each $R_{32}$ is hydrogen, unsubstituted alkyl, or substituted alkyl; each $R^e$ is independently unsubstituted alkyl, substituted alkyl, unsubstituted alkenyl, unsubstituted alkenyl, unsubstituted alkynyl, substituted alkynyl, unsubstituted alkoxy, substituted alkoxy, unsubstituted alkylamino, substituted alkylamino, unsubstituted dialkylamino, substituted dialkylamino, hydroxy, unsubstituted aryl, substituted aryl, unsubstituted heteroaryl, substituted heteroaryl, unsubstituted carboxyl, substituted carboxyl, unsubstituted amino, substituted amino, unsubstituted amido, substituted amido, unsubstituted $C_3$-$C_{20}$ cyclic, substituted $C_3$-$C_{20}$ cyclic, unsubstituted $C_3$-$C_{20}$ heterocyclic, or substituted $C_3$-$C_{20}$ heterocyclic; y is an integer between 0 and 11, inclusive; $R_{25}$, $R_{26}$, $R_{27}$, $R_{28}$, $R_{29}$, and $R_{30}$ are independently C or N, wherein the bonds between adjacent $R_{25}$ to $R_{30}$ are double or single according to valency, and wherein $R_{25}$ to $R_{30}$ are bound to none, one, or two hydrogens according to valency, or Az can be

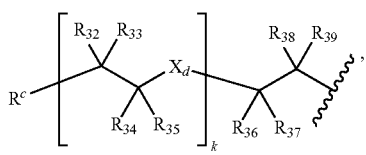

Formula XV wherein in Formula XV of Az, $R_{32}$, $R_{33}$, $R_{34}$, $R_{35}$, $R_{36}$, $R_{37}$, $R_{38}$, and $R_{39}$ are independently hydrogen, unsubstituted alkyl, substituted alkyl, unsubstituted alkenyl, substituted alkenyl, unsubstituted alkynyl, substituted alkynyl, unsubstituted phenyl, substituted phenyl, unsubstituted aryl, substituted aryl, unsubstituted heteroaryl, substituted heteroaryl, unsubstituted arylalkyl, substituted arylalkyl, unsubstituted alkoxy, substituted alkoxy, unsubstituted aroxy, substituted aroxy, unsubstituted carbonyl, substituted carbonyl, unsubstituted carboxyl, substituted carboxyl, unsubstituted amino, substituted amino, unsubstituted amido, substituted amido, unsubstituted $C_3$-$C_{20}$ cyclic, substituted $C_3$-$C_{20}$ cyclic, unsubstituted $C_3$-$C_{20}$ heterocyclic, substituted $C_3$-$C_{20}$ heterocyclic, poly(ethylene glycol), or poly(lactic-co-glycolic acid); k is an integer from 0 to 20; each $X_d$ is independently absent, O, or S; and $R^c$ is Bz.

In some forms of Formula XIII and Formula XV, wherein Bz can be

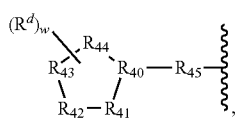

Formula XVI wherein for Formula XVI of Bz, $R_{45}$ is —$(CR_{46}R_{46})_p$—; p is an integer from 0 to 5; each $R_{46}$ is hydrogen, unsubstituted alkyl, or substituted alkyl; each $R^d$ is independently unsubstituted alkyl, substituted alkyl, unsubstituted alkenyl, unsubstituted alkenyl, unsubstituted alkynyl, substituted alkynyl, unsubstituted alkoxy, substituted alkoxy, unsubstituted alkylamino, substituted alkylamino, unsubstituted dialkylamino, substituted dialkylamino, hydroxy, unsubstituted aryl, substituted aryl, unsubstituted heteroaryl, substituted heteroaryl, unsubstituted carboxyl, substituted carboxyl, unsubstituted amino, substituted amino, unsubstituted amido, substituted amido, unsubstituted $C_3$-$C_{20}$ cyclic, substituted $C_3$-$C_{20}$ cyclic, unsubstituted $C_3$-$C_{20}$ heterocyclic, or substituted $C_3$-$C_{20}$ heterocyclic; w is an integer between 0 and 4, inclusive; each $R_{40}$, $R_{41}$, $R_{42}$, $R_{43}$, and $R_{44}$, are independently C or N, wherein the bonds between adjacent $R_{40}$ to $R_{44}$ are double or single according to valency, and wherein $R_{40}$ to $R_{44}$ are bound to none, one, or two hydrogens according to valency.

In some forms of Formula XIII, Cz can be

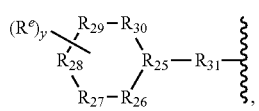

Formula XIV wherein in Formula XIV of Cz, $R_{31}$ is —$(CR_{32}R_{32})_p$— or —$(CR_{32}R_{32})_p$—$X_b$—$(CR_{32}R_{32})_q$—; p and q are independently integers between 0 to 5, inclusive; each $R_{32}$ is hydrogen, unsubstituted alkyl, or substituted alkyl; $X_b$ is absent, —O—, —S—, —S(O)—, —S(O)$_2$—, or N$R_{47}$; $R_{47}$ is unsubstituted alkyl or substituted alkyl; each $R^e$ is independently unsubstituted alkyl, substituted alkyl, unsubstituted alkenyl, unsubstituted alkenyl, unsubstituted alkynyl, substituted alkynyl, unsubstituted alkoxy, substituted alkoxy, unsubstituted alkylamino, substituted alkylamino, unsubstituted dialkylamino, substituted dialkylamino, hydroxy, unsubstituted aryl, substituted aryl, unsubstituted heteroaryl, substituted heteroaryl, unsubstituted carboxyl, substituted carboxyl, unsubstituted amino, substituted amino, unsubstituted amido, substituted amido, unsubstituted $C_3$-$C_{20}$ cyclic, substituted $C_3$-$C_{20}$ cyclic, unsubstituted $C_3$-$C_{20}$ heterocyclic, or substituted $C_3$-$C_{20}$ heterocyclic; y is an integer between 0 and 11, inclusive; $R_{25}$, $R_{26}$, $R_{27}$, $R_{28}$, $R_{29}$, and $R_{30}$ are independently C or N, wherein the bonds between adjacent $R_{25}$ to $R_{30}$ are double or single according to valency, and wherein $R_{25}$ to $R_{30}$ are bound to none, one, or two hydrogens according to valency.

In some forms, for Formula XIV of Az, each $R_{32}$ is hydrogen, and p is 1.

In some forms, for Formula XIV of Az, each $R_{32}$ is hydrogen, p is 1, $R_{25}$ is C, and $R_{26}$-$R_{30}$ are CH, and the bonds between $R_{25}$ and $R_{26}$, between $R_{27}$ and $R_{28}$, and between $R_{29}$ and $R_{30}$ are double bonds.

In some forms, for Formula XIV of Az, each $R_{32}$ is hydrogen, p is 1, $R_{25}$ is C, and $R_{26}$-$R_{30}$ are CH, and the bonds between $R_{25}$ and $R_{26}$, between $R_{27}$ and $R_{28}$, and between $R_{29}$ and $R_{30}$ are double bonds, and y is 1.

In some forms, for Formula XIV of Az, each $R_{32}$ is hydrogen, p is 1, $R_{25}$ is C, and $R_{26}$-$R_{30}$ are CH, and the bonds between $R_{25}$ and $R_{26}$, between $R_{27}$ and $R_{28}$, and between $R_{29}$ and $R_{30}$ are double bonds, y is 1, and $R^e$ is Bz having Formula XVI.

In some forms, for Formula XIV of Az, each $R_{32}$ is hydrogen, p is 1, $R_{25}$ is C, and $R_{26}$-$R_{30}$ are CH, and the bonds between $R_{25}$ and $R_{26}$, between $R_{27}$ and $R_{28}$, and between $R_{29}$ and $R_{30}$ are double bonds, y is 1, and for Formula XVI of Bz, p is 0.

In some forms, for Formula XIV of Az, each $R_{32}$ is hydrogen, p is 1, $R_{25}$ is C, and $R_{26}$-$R_{30}$ are CH, and the bonds between $R_{25}$ and $R_{26}$, between $R_{27}$ and $R_{28}$, and between $R_{29}$ and $R_{30}$ are double bonds, y is 1, and for Formula XVI of Bz, p is 0, and $R_{40}$-$R_{42}$ are N.

In some forms, for Formula XIV of Az, each $R_{32}$ is hydrogen, p is 1, $R_{25}$ is C, and $R_{26}$-$R_{30}$ are CH, and the bonds between $R_{25}$ and $R_{26}$, between $R_{27}$ and $R_{28}$, and between $R_{29}$ and $R_{30}$ are double bonds, y is 1, and for Formula XVI of Bz, p is 0, $R_{40}$-$R_{42}$ are N, and $R_{43}$ and $R_{44}$ are C.

In some forms, for Formula XIV of Az, each $R_{32}$ is hydrogen, p is 1, $R_{25}$ is C, and $R_{26}$-$R_{30}$ are CH, and the bonds between $R_{25}$ and $R_{26}$, between $R_{27}$ and $R_{28}$, and between $R_{29}$ and $R_{30}$ are double bonds, y is 1, and Formula XVI of Bz, is

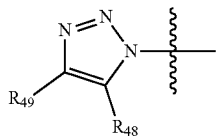

Formula XVII wherein $R_{48}$ and $R_{49}$ are independently hydrogen,

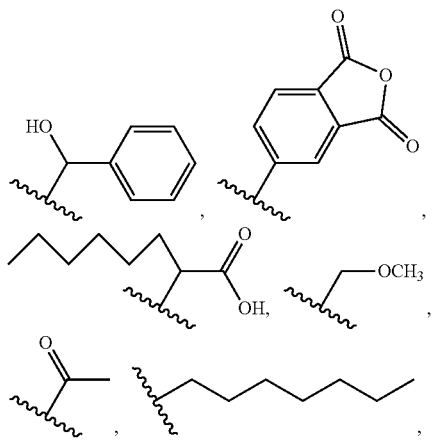

or Cz having Formula XIV, preferably wherein $R_{48}$ and $R_{49}$ are not both hydrogen.

In some forms, for Formula XIV of Cz, $R_{31}$ is —$(CR_{32}R_{32})_p$—$X_b$—$(CR_{32}R_{32})_q$—, each $R_{32}$ is hydrogen, and p is 0.

In some forms, for Formula XIV of Cz, $R_{31}$ is —$(CR_{32}R_{32})_p$—$X_b$—$(CR_{32}R_{32})_q$—, each $R_{32}$ is hydrogen, p is 0, and q is 1.

In some forms, for Formula XIV of Cz, $R_{31}$ is —$(CR_{32}R_{32})_p$—$X_b$—$(CR_{32}R_{32})_q$—, each $R_{32}$ is hydrogen, p is 0, q is 1, and $X_b$ is O or —S(O)$_2$—.

In some forms, for Formula XIV of Cz, $R_{31}$ is —$(CR_{32}R_{32})_p$—$X_b$—$(CR_{32}R_{32})_q$—, each $R_{32}$ is hydrogen, p is 0, q is 1, $X_b$ is O, and $R_{26}$ is O.

In some forms, for Formula XIV of Cz, $R_{31}$ is —$(CR_{32}R_{32})_p$—$X_b$—$(CR_{32}R_{32})_q$—, each $R_{32}$ is hydrogen, p is 0, q is 1, $X_b$ is O, $R_{26}$ is O, and $R_{25}$ is CH.

In some forms, Formula XIV of Cz is

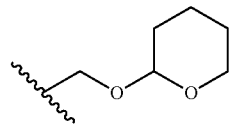

In some forms, of Formula XIII, Az can be

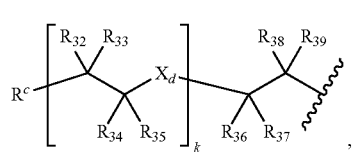

Formula IX

As defined above, and $R^c$ is Bz having Formula XVI, as defined above.

In some forms, for Formula IX of Az, Xd is O.

In some forms, for Formula IX of Az, Xd is O, and $R_{32}$-$R_{39}$ are hydrogen.

In some forms, for Formula IX of Az, Xd is O, $R_{32}$-$R_{39}$ are hydrogen, and k is an integer between 1 and 5, inclusive, preferably 3.

In some forms, for Formula XVI of Bz, p is 0.

In some forms, for Formula XVI of Bz, p is 0, and $R_{40}$-$R_{42}$ are N.

In some forms, for Formula XVI of Bz, p is 0, $R_{40}$-$R_{42}$ are N, and $R_{43}$ and $R_{44}$ are C.

In some forms, Formula XVI of Bz is

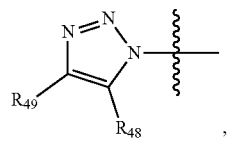

Formula XVII wherein $R_{48}$ and $R_{49}$ are independently hydrogen,

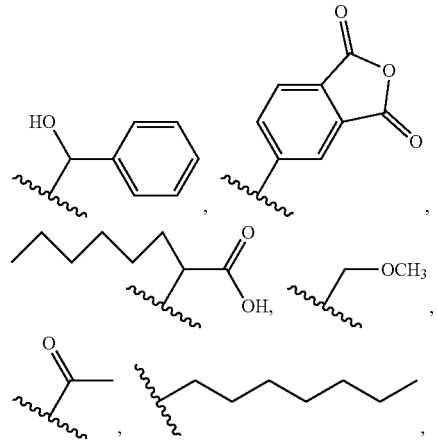

or Cz having Formula XIV, preferably wherein $R_{48}$ and $R_{49}$ are not both hydrogen.

In some forms, for Formula XIV of Cz, $R_{31}$ is —$(CR_{32}R_{32})_p$—, each $R_{32}$ is hydrogen, p is 0 or 1.

In some forms, for Formula XIV of Cz, $R_{31}$ is $-(CR_{32}R_{32})_p-$, each $R_{32}$ is hydrogen, p is 1, and $R_{25}$ is N.

In some forms, for Formula XIV of Cz, $R_{31}$ is $-(CR_{32}R_{32})_p-$, each $R_{32}$ is hydrogen, p is 1, $R_{25}$ is N, and $R_{28}$ is $S(O)_2$.

In some forms, for Formula XIV of Cz, $R_{31}$ is $-(CR_{32}R_{32})_p-$, each $R_{32}$ is hydrogen, p is 1, $R_{25}$ is N, $R_{28}$ is $S(O)_2$, and $R_{26}$, $R_{27}$, $R_{29}$, and $R_{30}$ are $CH_2$.

In some forms, Formula XIV of Cz is

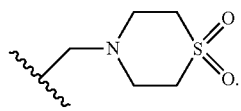 [SMILES: *CN1CCS(=O)(=O)CC1]

In some forms, for Formula XIV of Cz, $R_{31}$ is $-(CR_{32}R_{32})_p-$, each $R_{32}$ is hydrogen, p is 0, $R_{25}$ is C, $R_{26}$-$R_{30}$ are CH, and the bonds between $R_{25}$ and $R_{26}$, between $R_{27}$ and $R_{28}$, and between $R_{29}$ and $R_{30}$ are double bonds.

In some forms, for Formula XIV of Cz, $R_{31}$ is $-(CR_{32}R_{32})_p-$, each $R_{32}$ is hydrogen, p is 0, $R_{25}$ is C, $R_{26}$-$R_{30}$ are CH, the bonds between $R_{25}$ and $R_{26}$, between $R_{27}$ and $R_{28}$, and between $R_{29}$ and $R_{30}$ are double bonds, and y is 1.

In some forms, for Formula XIV of Cz, $R_{31}$ is $-(CR_{32}R_{32})_p-$, p is 0, $R_{25}$ is C, and $R_{26}$-$R_{30}$ are CH, the bonds between $R_{25}$ and $R_{26}$, between $R_{27}$ and $R_{28}$, and between $R_{29}$ and $R_{30}$ are double bonds, y is 1, and $R^e$ is $-NH_2$.

In some forms, Formula XIV of Cz is

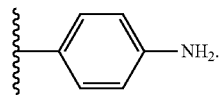

In some forms, the chemical moiety can be

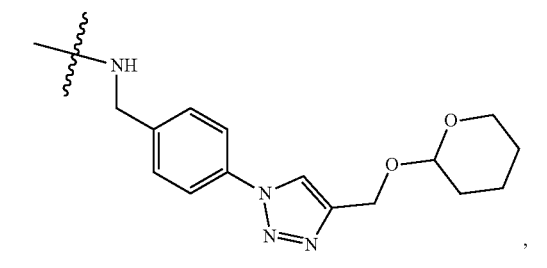
E9 (Z2-Y12)

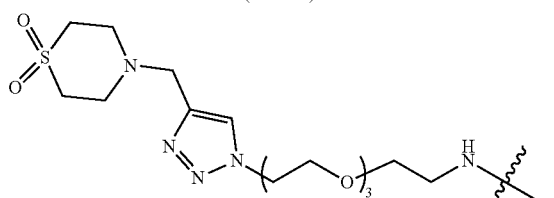
RZA (Z1-Y15)

-continued

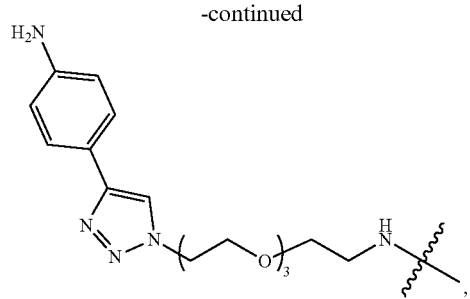
Z1-Y19 and combinations thereof.

III. Methods of Making

A. Small Molecules

Useful small molecules include, but are not limited to, alcohols, thiols, amines, and combinations thereof.

1. Alcohols

Preferred alcohols for use as reagents in esterification include those shown below.

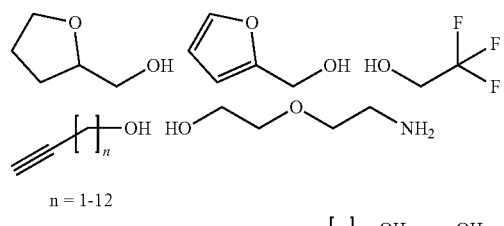

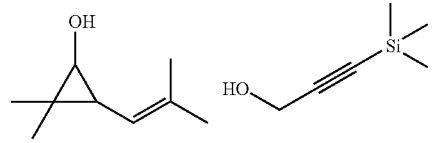

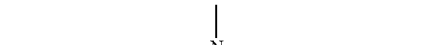

2. Amines

Preferred amines that can be used to modify the surfaces of the products include, but are not limited to,

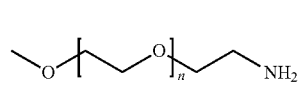

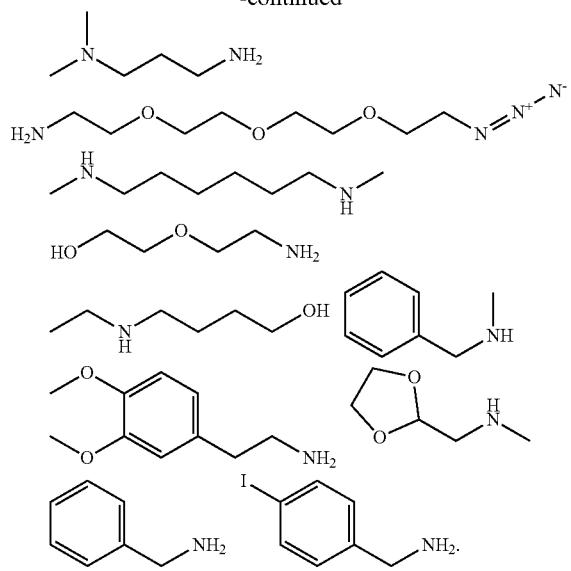

3. Derivatization Via Click Chemistry

In some forms, the surfaces of the neurological implants are covalently modified initially to introduce a functional group which can be further reacted via click chemistry.

In preferred embodiments, the alcohols, amines or thiols are used to introduce a functional group which can further reacted using a 1,3-dipolar cycloaddition reaction (i.e., a Huisgen cycloaddition reaction). In a 1,3-dipolar cycloaddition reaction, a first molecule containing an azide moiety is reacted with a second molecule containing a terminal or internal alkyne. As shown below, the azide and the alkyne groups undergo an intramolecular 1,3-dipolar cycloaddition reaction, coupling the two molecules together and forming a 1,2,3-triazole ring.

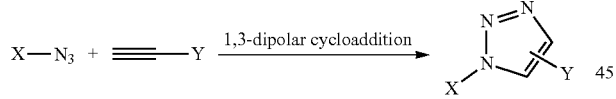

The regiochemistry of 1,3-dipolar cycloadditions reaction can be controlled by addition of a copper(I) catalyst (formed in situ by the reduction of $CuSO_4$ with sodium ascorbate) or a ruthenium catalyst (such as Cp*RuCl(PPh$_3$)$_2$, Cp*Ru (COD), or Cp*[RuCl$_4$]). For example, using a copper catalyst, azides and terminal alkynes can be reacted to exclusively afford the 1,4-regioisomers of 1,2,3-triazoles. Similarly, in the presence of a suitable ruthenium catalyst, azides can be reacted with internal or terminal alkynes to form exclusively the 1,5-regioisomers of 1,2,3-triazoles.

In some forms, the alcohol, amine or thiol containing an alkyne moiety is used to modify the surface initially. In these forms, the alkyne moiety present on the surface can be further reacted with a second molecule containing an azide functional group. Upon reaction, the azide and the alkyne groups undergo an intramolecular 1,3-dipolar cycloaddition reaction forming a 1,2,3-triazole ring, coupling the second molecule to the covalently modified surface.

In some forms, the small molecules are synthesized and these used post-synthesis to modify the surface of the neurological implants. In some forms, the small molecules are synthesized using the alcohols, amines, and alkynes described herein. Examples of small molecules that can be used to modify the surface of the neurological implants include, but are not limited to small molecules that contain a substituted heteroaryl group such as,

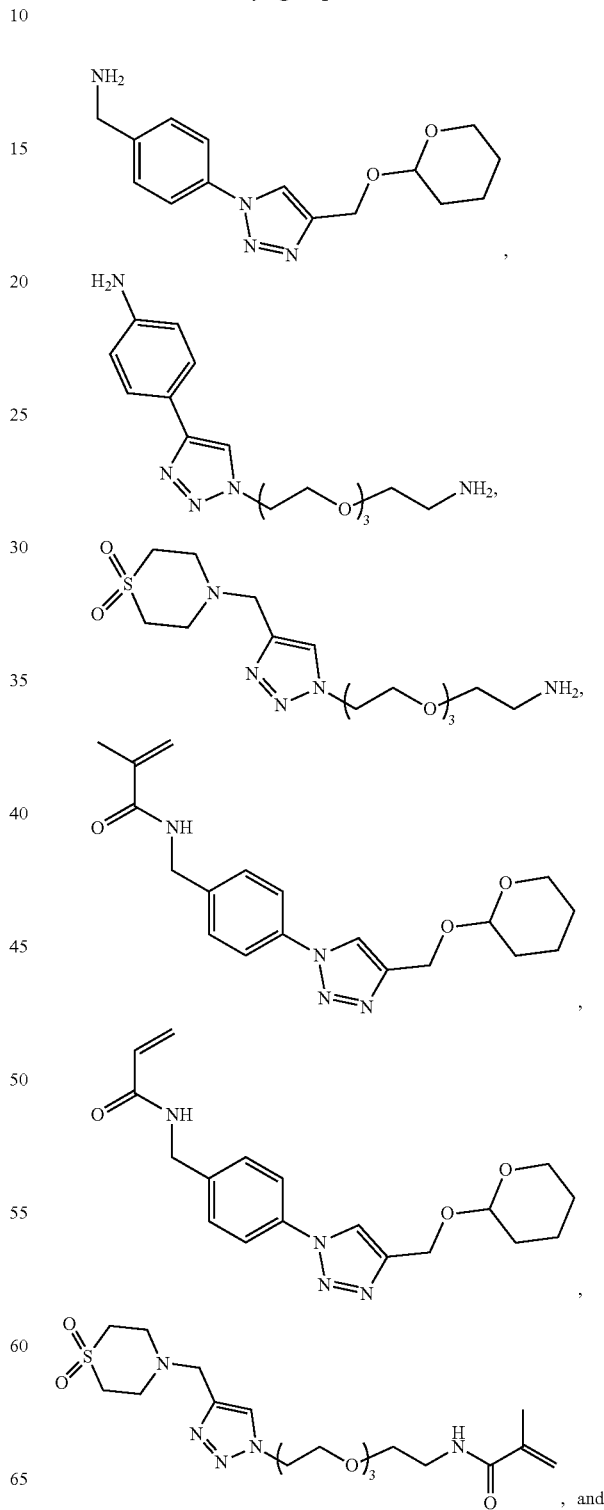

-continued

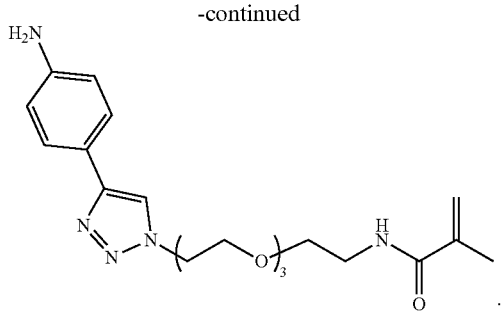

B. Implants
1. Implants Having Chemical Moieties Dispersed Therein and Thereon
a. Small Molecule Coatings for Implants The small molecules or chemical moieties described herein can be used for chemically modifying a surface of the implants and can be covalently (directly or indirectly) or non-covalently associated with a surface of the implants. Preferably, the small molecules are covalently associated with a surface of the implants.

In some forms, prior to chemically modifying a surface of the implants, the surface can be functionalized by treating the surface with plasma. The surface of the neurological implant can be functionalized by introducing functional groups such as hydroxyl, carboxyl, ester, aldehyde, ketone, carbonate, nitrile, amine, imine, amide, imide, etc., depending on the type of gas used to generate the plasma. For example, oxygen plasma can lead to the introduction of hydroxyl, carboxyl, ester, aldehyde, ketone, and carbonate functional groups to the surface of the implant.

In some forms, before or after treatment of the surface with plasma, the surface can be functionalized with an epoxy-silane (3-glycidoxypropyl-trimethoxy-silane) via chemical vapor deposition. After functionalization, the small molecule can be reacted with a group on the -glycidoxypropyl-trimethoxy-silane, such as the glycidyl group, to introduce a chemical moiety described herein onto the surface.

The surfaces of the implants can be chemically modified to any desired density of modifications. The density of modifications is the average number of modifications (that is, attached compounds) per a given area of the surface or a surface of the neurological implant. Generally, a density at or above a threshold density can provide a beneficial effect, such as lower foreign body response. In some forms, a high density is not required. Without being bound to any particular theory of operation, it is believed that the chemical modifications signal to, indicate to, or are identified by, one or more immune system or other body components to result in a beneficial effect, such as a lower foreign body response. In some forms, a lower density of modifications can be effective for this purpose.

Useful densities include densities of at least, of less than, of about, or of 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 320, 340, 360, 380, 400, 420, 440, 460, 480, 500, 550, 600, 650, 700, 750, 800, 850, 900, and 1000 modifications per square μm. All ranges defined by any pair of these densities are also specifically contemplated and disclosed.

In some forms, the density of the modifications on a surface, surfaces, or portions of a surface(s) of a neurological implant that, when the neurological implant is administered to (e.g., implanted in the body of) a subject, would be in contact with fluid(s), cell(s), tissue(s), other component(s), or a combination thereof of the subject's body is greater than the density of the modifications on other surfaces of the neurological implant.

Density can also be expressed in terms of the concentration of the surface modifications as measured by X-ray photoelectron spectroscopy (XPS). XPS is a surface-sensitive quantitative spectroscopic technique that measures the elemental composition at the parts per thousand range of the elements that exist within a material. XPS spectra are obtained by irradiating a material with a beam of X-rays while simultaneously measuring the kinetic energy and number of electrons that escape from the top 0 to 10 nm of the material being analyzed. By measuring all elements present on the surface, the percentage of the elements that come from the surface modifications can be calculated. This can be accomplished by, for example, taking the percentage of nitrogen (and/or other elements in the surface modifications) in the total elemental signal measured. Nitrogen can be a useful indicator for the surface modification, especially when many substrates and materials forming the neurological implants contain little nitrogen. For convenience, the percent of the element(s) used to indicate the surface modifications can be stated as the percent surface modifications. Also for convenience, the percent surface modifications can be referred to as the concentration of surface modifications. Examples of XPS analysis and concentrations of surface modifications are shown in Tables 4-7.

Useful percent surface modifications include concentrations of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, and 100 percent surface modifications. All ranges defined by any pair of these concentrations are also specifically contemplated and disclosed.

The one or more layers on the surface can have a thickness between 10 nm and 1 mm, as measured using an analytical method such as ellipsometry or light microscopy. Useful thickness include dimensions of about 10 nm, 15 nm, 20 nm, 50 nm, 75 nm, 100 nm, 125 nm, 150 nm, 200 nm, 250 nm, 500 nm, 750 nm, 1,000 nm, 1,500 nm, 2,000 nm, 10 μm, 50 μm, 100 μm, 150 μm, 250 μm, 300 μm, 500 μm, 750 μm, 1 mm.

b. Functionalized Polymers for Implant Coatings or for Forming Implants

In some instances, the small molecules or chemical moieties described herein are covalently coupled (functionalized) onto a suitable polymer backbone which can coat and/or be covalently bound to a surface of an implant or medical device. The polymers may be homopolymers, copolymers, or dendrimers (such as PAMAM). The polymer is chosen based on a desired functional group which can be used to couple the small molecules or chemical moieties to the polymer backbone or to a monomer(s) used to synthesize the functionalized polymer. Examples of suitable functional groups on the polymer which can be used to couple with the small molecules or chemical moieties include, but are not limited to, amines, carboxylic acids, epoxides, azides, alkynes, vinyl groups, and aldehydes. As discussed above, the small molecules or chemical moieties may include functional groups such as alcohols, amines, and alkynes which react with the functional groups on the polymer to form functionalized polymers.

In some embodiments, functionalized polymers can be coated onto a substrate grafted to a substrate, such as a catheter or other implantable medical device, using a variety of techniques known in the art. This may be done, for example, by spray coating, dip coating, or brush coating the functionalized polymer to form one or more coatings on the surface(s) of the substrate. The coatings or films can each, alone or combined, have a thickness less than about 1000 nm, 750 nm, 500 nm, 250 nm, 100 nm, 50 nm, 25 nm, or 10 nm and can be applied to substrates of any size, shape, composition, and complexity.

In some instances, the functionalized polymers can be grafted onto a substrate, such as a catheter, shunt, or other implantable medical device, using a variety of techniques known in the art. The implantable medical device, such as a catheter, may be formed from polymers, such as, but not limited to poly(dimethylsiloxane), polyurethane, or silicone. The implantable medical device, such as a catheter, may be formed from metal and metal alloys, such as, but not limited to titanium, gold, or platinum. For example, the functionalized polymer can be synthesized and then coupled to the surface of the device. The polymer can also be grown from the surface of the device. The polymer can be grown in solution or from the substrate using a variety of polymerization techniques including, but not limited to, free radical polymerization, anionic polymerization, cationic polymerization, and enzymatic polymerization. In some embodiments, a polymer may be grafted/attached to the surface of an implantable device and subsequently functionalized with the small molecules or chemical moieties by reacting with functional groups present on the polymer.

Suitable polymers which can be functionalized to include small molecules or chemical moieties therein include, but are not limited to, poly(dimethylsiloxane), poly(lactone), poly(olefins), poly(anhydride), poly(urethane), poly(acrylates), poly(orthoester), poly(ethers), poly(esters), poly(phosphazine), poly(ether ester)s, poly(amino acids), synthetic poly(amino acids), poly(carbonates), poly(hydroxyalkanoate)s, alginates, zwitterionic polymers (such as polymers containing sulfobetaine or carboxybetaine moieties), polysaccharides, cellulosic polymers, gelatin, collagen, and blends and copolymers thereof.

The functionalized polymers are attached to implants, such as poly(dimethylsiloxane), silicone, or polyurethane, which are commonly used to make catheters, shunts, or other implantable medical devices.

In some instances, the functionalized polymer can form a polymer brush. The growth of polymer brushes typically requires the presence of vinyl moieties on the implant. In order to introduce vinyl groups onto the surface of substrates, a suitable substrate, such a silicone, can be treated, for example, with a pure oxygen plasma followed by emersion in ethanol to create a surface that is purely hydroxyl in nature. Following hydroxylation, the surface can be exposed to an evaporated vinyl silane, such as trichlorovinyl silane or trimethoxy-vinyl silane. The vinylated substrate can then be used to attach brush polymers. Polyurethane substrates can be treated in an analogous manner, for example, using a plasma treatment with $CO_2$, $O_2$, ammonia. The resulting hydroxyl and/or amine groups can be acrylated to form vinyl moieties on the surface followed by tethering of the polymer brushes. Polymer brushes can have reactive functional groups, such as amines, at surface concentrations 10-100 times higher than those possible through direct surface functionalization.

In certain embodiments, functionalized reactive monomers can be polymerized directly onto a substrate, such as a catheter or shunt or other implantable medical device made of plastic and/or metal, using techniques such as chemical vapor deposition. Chemical vapor deposition (CVD) is a process by which a thin film is deposited directly from the gas phase onto a substrate. The polymer can be deposited using plasma/microwave CVD, hot filament CVD, initiated CVD, and photo-initiated CVD. In one embodiment, a polymerizable monomer and a free radical initiator are fed simultaneously into a CVD reaction chamber containing a hot filament to form a thin polymer film of controlled chemistry. Within the chamber, the radical initiator is activated by a resistively heated filament. The resulting radicals react with monomer molecules which have absorbed onto the substrate surface to form the thin polymer film. CVD can be used to coat substrates of all shapes and almost any composition with a high degree of conformation.

Silicone polymers (such as poly(dimethylsiloxane) and copolymers containing silicone segments, such as polydialkylsiloxane, wherein the alkyl substituent can be dimethyl, diethyl, dipropyl, dibutyl and so on can contain reactive functional end groups. Reactive functional end groups can include an alkyl amine, hydroxyl, carboxylic acid or aldehyde. Such functional end groups can be reacted and coupled the small molecules or chemical moieties described herein to afford siloxanes which are terminal end functionalized. In one example, the reactive functional end groups are carboxylic acids which can be coupled to the amine group of a small molecule or chemical moiety described resulting in attachment of the small molecule or chemical moiety to the end groups of the siloxane polymer. The terminal end functionalized siloxanes can be used to form implantable devices and/or can be cast, such as in molds or 3-D printed, to form an implantable medical devices, such as a catheter or shunt.

In certain instances, silicone polymers (such as poly(dimethylsiloxane) and silicone-containing polymer segments can be synthesized to include one or more pendant groups according to known methods. A non-limiting example of a siloxane polymer having a reactive one or more reactive pendant groups include a polymer according to the following structure:

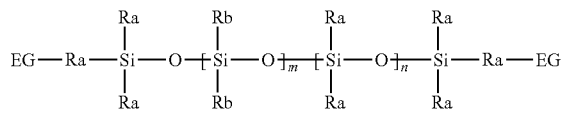

wherein n can range from 5 to 1000, 5 to 500 and m can range from 1 to 100, 1 to 50, or 1 to 25; EG is an end group such as hydrogen or a reactive functional group which can be a primary amine, secondary amine, hydroxyl, carboxylic acid, aldehyde, or carbamate; each $R_a$ is independently an aliphatic chain or aryl, substituted or unsubstituted, preferably an alkyl such as methyl, ethyl, propyl and butyl; at least one of the $R_b$ groups is a reactive functional pendant group, such as a vinyl group, a primary amine, secondary amine, hydroxyl, carboxylic acid, aldehyde, or carbamate and the other $R_b$ may be an aliphatic chain or aryl, substituted or unsubstituted, preferably an alkyl such as methyl, ethyl, propyl and butyl. Such functional pendant groups can be reacted and coupled the small molecules or chemical moieties described herein to afford siloxanes which are functionalized with the small molecules or chemical moieties described herein along the backbone. In one example, $R_b$ may be a vinyl group which reacts with the amine group of a small molecule or chemical moiety described resulting in attachment of the small molecule or chemical moiety to the siloxane backbone. These polymers may also be functionalized at the end groups as discussed. The pendant functionalized siloxanes can be used to form implantable devices and/or can be cast, such as in molds or 3-D printed, to form an implantable medical devices, such as a catheter or shunt.

In certain embodiments, functionalized reactive monomers, such as acrylates, are synthesized which contain the small molecules or chemical moieties. One non-limiting example includes the formation of an acrylate monomer:

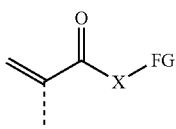

wherein the dashed line represents an optional methyl group, X may be —O— or —NH—, and FG is a reactive functional group which is small molecule or chemical moiety, as described above, which is bound to the acrylate group. Exemplary functionalized monomers may include:

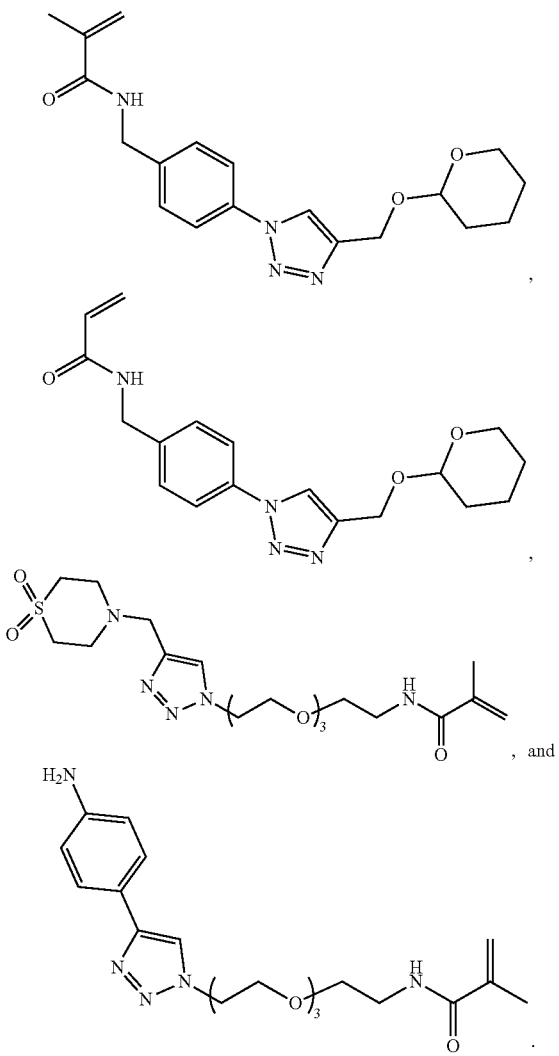

, and

Other types of polymerizable groups may be used and functionalized to include small molecule or chemical moieties coupled there to using known chemical techniques.

The reactive functionalized monomers may be used to form oligomers, polymers, copolymers, or blends thereof using known polymerization techniques. Copolymers may be formed of functionalized and unfunctionalized monomers. The resulting functionalized oligomers, polymers, copolymers typically contain small molecules or chemical moieties, typically as side groups and/or end groups. The weigh average molecular weights of the functionalized polymers may be from 1000 Da to 500,000 Da, 1000 Da to 250,000 Da, 1000 Da to 100,000 Da, 1000 Da to 50,000 Da, 1000 Da to 25,000 Da or 1000 Da to 10,000 Da.

The functionalized reactive monomers can be used to form functionalized polymers which can be cast, such as in molds or 3-D printed, to form an implantable medical devices, such as a catheter or shunt. Alternatively the functionalized reactive monomers may be cast in a mold and polymerized to form an implantable device directly (by exposure to appropriate conditions, such as heat, initiation, ultraviolet exposure). The functionalized monomers or blends may include crosslinkable (i.e., include crosslinkable compounds or moieties) which allow for the resulting functionalized polymer to be cast and cured to form a polymer-based implantable medical device, such as a catheter or shunt, having small molecule or chemical moieties therein and/or thereon. In such cases, where an implantable medical device, such as a catheter or shunt, is formed from functionalized polymer or blends of such polymers the mall molecules or chemical moieties are dispersed throughout the device (i.e., within and on the surfaces of the device). Without being bound to any particular theory of operation, it is believed that implantable devices formed from functionalized polymer result in a beneficial effect, such as a lower foreign body response when implanted.

The functionalized polymers are biocompatible and may be degradable or non-degradable polymers. Devices, such as catheters or shunts which are formed from such functionalized polymers or blends or mixtures thereof can be tuned to have appropriate physical properties, such as degradation properties, elastic properties, hardness, etc.

IV. Methods of Using

The neurological implants can be used in acute and chronic applications that involve the restoration, replacement, or bypassing of lost neurological functions due to diseases or injuries to parts of the nervous system, e.g., the central nervous system (CNS). These include, but are not limited to, draining fluids in patients with hydrocephalus, microdialysis sampling, monitoring local ion concentrations, and CNS amperometry and/or voltammetry for electrophysiological recording.

The implants can be implanted as prosthesis, as pumps, cardiac leads, electrodes into the brain or as hearing or eye stimulators or conductors of nerve impulses. The devices are intended to be in abutment, in whole or in part, with nerve tissue. The anti-inflammatory molecules bound to or incorporated into the device help to reduce swelling and impairment of nerve function which is commonly associated with the implantation procedure. Although the anti-inflammatory may obviate the need for subsequent administration of anti-inflammatory locally or systemically, these may be administered at the time of implantation or later.

The methods, compounds, and compositions herein described are further illustrated in the following examples, which are provided by way of illustration and are not intended to be limiting. It will be appreciated that variations in proportions and alternatives in elements of the components shown will be apparent to those skilled in the art and are within the scope of disclosed forms. All parts or amounts, unless otherwise specified, are by weight.

EXAMPLES

Example 1: Chemical Modification of Neurological Implants and Characterization

Materials and Methods (i) Chemical Modification

Ventricular catheters, purchased from Medtronic, were chemically modified with anti-inflammatory small organic molecules termed E9 (Z2-Y12) and RZA15 (Z1-Y15). To perform chemical modifications, the catheters were plasma treated for 1 min on each side and immediately dropped into a 0.2-M solution of either E9 or RZA15 in 5% DMSO in toluene. The reaction was stirred for 60 min and the materials were washed three times in methanol, three times in ethanol, three times with sterile grade water, and finally again with sterile grade ethanol. The materials are dried under high vacuum overnight.

(ii) Characterization of Modified Surfaces (a) X-Ray Photoelectron Spectroscopy

X-ray photoelectron spectroscopy (XPS) is a surface-sensitive quantitative spectroscopic technique, which enables the measurement of the elemental composition at the surface (within 6 nm range) of a material with parts per thousand-range sensitivity. PHI Versaprobe II XPS equipped with a C60 cluster-ion gun as well as a floating voltage argon single-ion gun for depth profiling was employed for this study. A survey technique at 1100 eV, 200 µm spot size, 50-W, 15-kV ion gun neutralization was employed to perform the analysis. XPS analysis was performed on E9 and RZA15 surface-modified catheters. A catheter whose surface had not been chemically modified was used as a control.

Small pieces of each catheter were measured in three different spots and the average composition of each spot was used as the total atomic composition. The 1s transitions of carbon, oxygen, and nitrogen and the 2p transition of silica was used as a measure for atomic concentration.

(b) Scanning Electron Microscopy

Scanning electron microscopy (SEM) was used to determine the whether modifying the surfaces of the catheters with E9 and RZA15 produced any surface damage or pits. SEM analysis was performed on a catheter whose surface had not been chemically modified, as the control. For analysis we used a Jeol 5600LV Scanning Electron Microscope to examine shunt surfaces.

Results (a) X-Ray Photoelectron Spectroscopy

Following application of the E9 and RZA15 coatings, the surface chemistry of the catheters was characterized by XPS and SEM to determine whether the application methods used had produced conformal coatings of E9 and RZA15 on the clinical grade catheters.

The catheters with modified surfaces showed a 5.24±1.13% (RZA15) and 6.28±1.62% (E9) atomic concentration of elemental nitrogen on their surfaces. The XPS of the unmodified catheters showed only 1.16±0.27% atomic concentration of elemental nitrogen on the surface, which is close to the detection limit of the machine. The atomic concentrations of elements on the surface of the unmodified, RZA15-, and E9-modified catheters are shown in Tables 1, 2, and 3, respectively. These show that there is a significantly higher amount of elemental nitrogen on the surface of the RZA15- or E9-modified catheters compared to the unmodified catheters. The high amount of elemental nitrogen can only be caused by the modification with these chemical moieties, demonstrating successful modification of the surface of the catheters with RZA15 or E9.

TABLE 1

Atomic concentration table of unmodified catheter

| C1s | N1s | O1s | Si2p | |
|---|---|---|---|---|
| 0.314 | 0.499 | 0.733 | 0.368 | RSF |
| 57.912 | 90.720 | 128.622 | 79.836 | Corrected RSF |
| 49.72 | 1.25 | 29.19 | 19.84 | Catheter 1 |
| 49.28 | 0.86 | 28.43 | 21.44 | Catheter 2 |
| 48.73 | 1.39 | 29.15 | 20.74 | Catheter 3 |
| 49.24 | 1.16 | 28.92 | 20.67 | Mean |
| 0.50 | 0.27 | 0.43 | 0.80 | Standard Deviation |

TABLE 2

Atomic concentration table of RZA15-modified catheter

| C1s | N1s | O1s | Si2p | |
|---|---|---|---|---|
| 0.314 | 0.499 | 0.733 | 0.368 | RSF |
| 57.912 | 90.720 | 128.622 | 79.836 | Corrected RSF |
| 47.66 | 4.76 | 31.28 | 16.30 | Catheter 1 |
| 56.06 | 6.53 | 24.63 | 12.78 | Catheter 2 |
| 46.49 | 4.44 | 31.09 | 17.98 | Catheter 3 |
| 50.07 | 5.24 | 29.00 | 15.69 | Mean |
| 5.22 | 1.13 | 3.78 | 2.66 | Standard Deviation |

TABLE 3

Atomic concentration table of E9-modified catheter

| C1s | N1s | O1s | Si2p | |
|---|---|---|---|---|
| 0.314 | 0.499 | 0.733 | 0.368 | RSF |
| 57.912 | 90.720 | 128.622 | 79.836 | Corrected RSF |
| 61.33 | 5.33 | 22.05 | 11.29 | Catheter 1 |
| 60.43 | 8.16 | 21.94 | 9.48 | Catheter 2 |
| 57.41 | 5.36 | 23.78 | 13.46 | Catheter 3 |
| 59.72 | 6.28 | 22.59 | 11.41 | Mean |
| 2.05 | 1.62 | 1.03 | 1.99 | Standard Deviation |

(b) Scanning Electron Microscopy

SEM analysis was performed on unmodified, RZA15 modified, and E9 modified catheters. An evaluation of the images showed that the modified surfaces were similar to the unmodified surfaces, i.e., the modification of the surfaces of the catheters did not introduce surface damage, or pitting.

Example 2: In Vivo Studies of Foreign Body Response to Chemically Modified Neurological Implants Neurological implants are devices used to restore, replace or bypass the lost neurological functions due to diseases or injuries. When these implants are inserted into neurological tissue, they directly interface with cells of the nervous system. This interaction leads to recruitment of microglia and astrocytes cells leading to inflammation, scar tissue formation and cell death. These deleterious responses affect the performance of the device and overall health of peripheral tissue.

The Langer/Anderson laboratory at Massachusetts Institute of Technology (MIT) has developed a library of super biocompatible anti-inflammatory small molecule coatings, which have been discovered through a broad in vivo screen of more than 1000 different chemistry formulations (PCT/US2016/059966, filed Nov. 1, 2016, which claims priority to U.S. Provisional Application No. 62/249,343, filed Nov. 1, 2015).

A subgroup of these coatings has now been proven to be effective in reducing cell attachment and host foreign body responses when evaluated in long-term intraperitoneal implants in mice and non-human primate animal models. This study represents the first testing of these compounds on intracranial implants.

It was hypothesized that these super biocompatible anti-inflammatory coating(s) could be applied to polymers such as clinical grade polydimethylsiloxane (PDMS) ventricular catheters to reduce rates of non-infectious ventricular catheter obstruction, thereby dramatically reducing shunt failure rates in the pediatric hydrocephalus population. The two primary goals of this study were: 1) To establish that the biocompatible anti-inflammatory coating(s) can be applied to the surface of clinical-grade PDMS ventricular catheters in a reliable and conformal fashion; and 2) To perform initial in vivo testing of these coated catheters (with standard clinical-grade ventricular catheters serving as controls) by implanting them into adult male New Zealand white rabbits.

Anti-inflammatory coatings were applied to PDMS catheters to improve their compatibility in vivo. Covalent coupling was confirmed using X-ray photoelectron spectroscopy (XPS). This is a surface-sensitive quantitative spectroscopic technique that enables the measurement of elemental composition at the parts per thousand ranges at the surface of materials. Additionally, Scanning Electron Microscopy (SEM) analysis of the coated catheters to ensure that their manipulation has not altered their surface topography.

These chemical surface modifications hypothesized to reduce the recruitment of astrocytes and microglia cells to neurological implants were evaluated in coated and uncoated neurological shunts in a New Zealand white rabbit intracranial implant model.

Materials and Methods

Methods for Chemical Modification and Analysis:

Ventricular catheters, purchased from Medtronic, were chemically modified with proprietary anti-inflammatory small organic molecules termed E9 and RZA15.

To perform chemical modifications, the catheters were plasma treated for 1 min on each side and immediately dropped into a 0.2 mol solution of either E9 or RZA15 in 5% DMSO in toluene. The reaction was stirred for 60 min and the materials were washed three times in methanol, three times in ethanol, three times with sterile grade water, and finally again with sterile grade ethanol. The materials were dried under high vacuum overnight. The ease of the chemistry involved in applying these coatings underscores the potential for the ultimate commercialization of this process. Following application of the anti-inflammatory small molecule coatings, the surface chemistry was verified by X-ray photoelectron spectroscopy and scanning electron microscopy allowing us to conclude that the application methods used had produced conformal coatings on the clinical grade catheters.

Macroscopic implants are modified with moiety comprising:

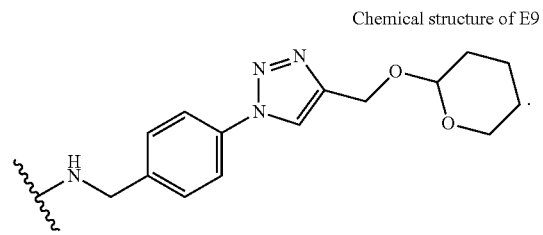

Chemical structure of E9

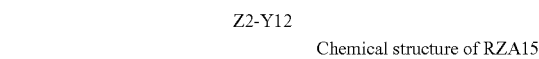

Z2-Y12

Chemical structure of RZA15

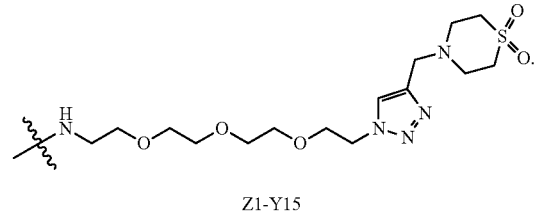

Z1-Y15

XPS analysis: X-ray photoelectron spectroscopy (XPS) is a surface-sensitive quantitative spectroscopic technique, which enables the measurement of the elemental composition at the surface (within 6 nm range) of a material with parts per thousand-range sensitivity. A PHI Versaprobe II XPS equipped with a C60 cluster-ion gun as well as a floating voltage argon single-ion gun for depth profiling were utilized. A Survey technique at 1100 eV, 200 μm spot size, 50 W 15 kV Ion gun neutralization was applied for the analysis. Small pieces of each catheter were measured in three different spots and the average composition of each spot was used as the total atomic composition. The is transitions of Carbon, Oxygen, and Nitrogen and the 2p transition of Silica was used as a measure for atomic concentration. RZA15 and E9 modification of the surface of the catheter was successful. The surfaces show a 5.24% (RZA15) and 6.28% (E9) concentration of nitrogen on the surface that can only be caused by the modification with the small molecules. As a control, the XPS of the blank catheters showed only 1.16% Nitrogen on the surface, which is close to the detection limit of the machine.

Rabbit Studies

Following establishment of an in vivo study protocol that demonstrated that a 12 mm catheter length was very efficient for bilateral implantation in adult male New Zealand white rabbits, a total of 10 rabbits were implanted with various combinations of unmodified, E9-modified, and RZA15-modified ventricular catheters. At two weeks post-implantation the rabbits were euthanized by way of whole animal perfusion fixation with 4% paraformaldehyde. After performing perfusion fixation the animals were decapitated and the heads were placed in containers containing 4% paraformaldehyde for 24 hrs ("post-fixation"). The heads were then transferred to buffer solution (PBS buffer with 90 mg/L sodium azide) and postmortem imaging was performed using a microcomputed tomography (microCT) scanner at the SCRI Small Animal Tomographic Analysis Facility confirming appropriate catheter trajectories.

After performing postmortem imaging of the rabbits' heads, the brains were carefully removed from the cranial vault, the implanted catheters were removed, and the brain parenchyma surrounding the catheter tracts was sectioned (12 μm thickness) using a cryostat. These brain sections were labeled using cell-specific markers for astrocytes (anti-glial fibrillary acidic protein) and microglia (anti-Iba1). These targets were visualized using Alexa 488 and Alexa 594 conjugated secondary antibodies; additionally a nuclear stain (DAPI) was applied. The sections were then imaged with an Olympus IX81 inverted microscope with a motorized x-y-z stage, broad-spectrum light source, and charge-coupled device camera (30× objective, 0.3-μm step size, 12-μm z-stack).

SEM Analysis:

Scanning electron microscopy (SEM) was used to determine if modifying surfaces anti-inflammatory molecules produces any surface damage or pits. SEM analysis was performed on unmodified, RZA modified, and E9 modified shunts. An evaluation of the images reveals no surface damage, or pitting. The modified surfaces appear similar to the unmodified surfaces.

Results

X-ray photoelectron spectroscopy (XPS) analysis of control unmodified, RZA15 modified, and E9 modified ventricular catheters confirmed successful attachment of anti-inflammatory molecules to the surface of the catheters.

SEM analysis of shunt surfaces of unmodified, RZA15 modified, and E9 modified ventricular catheters showed significant alterations to the surface after chemical modification.

Histologic examination of brain tissue around E9 coated catheter tracts revealed typical patterns of infiltrative immune cells, however, these cells were far less numerous that those seen in response to uncoated catheters. The effect seen with the RZA15 coating appears to be somewhat more distinct. Histologic examination of brain tissue around RZA15 coated catheters reveals the presence of both reduced inflammatory cell numbers as well as a disruption in the normal layers of inflammatory cells seen around implanted devices. It was hypothesized that these coatings cause tissue microglia to remain in a resting state phenotype, such that they do not produce the pro-inflammatory cytokines that promote astrocyte recruitment and activation.

These observations were quantified by maximum projections of the confocal z-stack images and using MetaMorph Microscopy Automation & Image Analysis Software (Molecular Devices, Sunnyvale, Calif.) to divide the maximum projections into 100-μm intervals from the catheter tract.

Computed tomography (CT) scan of rabbit head with bilateral 12 mm-long ventricular shunt catheters implanted was performed. A three-dimensional reconstruction of the CT scan slices was carried out. The bilateral burr holes were situated just anterior to the coronal suture, and radio-opaque catheter tips situated within the brain were observed as well. A single slice reconstruction in the sagittal plane was also generated. For clarity of the analysis, the anatomical terms of orientation were denoted on the image (rostral, caudal, dorsal, and ventral) being analyzed. Although there is some beam hardening artifact associated with the radio-opaque catheter tip, the resolution of this CT scan is sufficient to rule out the presence of any significant intraparenchymal hemorrhage associated with catheter insertion and provides verification of the appropriate catheter orientation/trajectory within the brain.

There are markedly fewer inflammatory cells around the catheter tracts at distances beyond 1 cm ($10^{th}$ 100-μm interval) for the E9- and RZA15-coated catheters as compared to the control catheters, with the RZA15-coated catheters in particular demonstrating reduced cell numbers reflective of an attenuated immune response. Reduced brain parenchymal inflammatory response to ventricular shunt catheters coated in E9 and RZA15 small molecules using representative confocal microscopy imaging demonstrating tissue responses to control, E9-, B'), and RZA15-coated catheters was observed. In all cases, the catheter tract could be identified as the dead space on the left of the image. All images represented maximum projections of confocal z-stacks obtained with an Olympus IX81 inverted microscope with a motorized x-y-z stage, broad-spectrum light source, and charge-coupled device camera (30× objective, 0.3-μm step size, 12-μm z-stack). One set of images were multi-channel overlays with glial fibrillary acidic protein (astrocytes), ionized calcium binding adaptor molecule 1 (microglia), and DAPI (nuclei). Another set of images demonstrated only the nuclear channel for ease of visualizing differences in cellular density with respect to distance from the catheter tract. Note that the control (uncoated) ventricular catheter generated a characteristic inflammatory infiltrate with a zone of densely packed microglia most intimately associated with the tract followed by a zone of reactive astrocytes. The E9-coated catheters demonstrated similar immune response architecture as compared to control catheters, however, the zone of high-density inflammatory cells did not extend as far from the catheter tract in the presence of the E9 coating. The RZA15-coated catheters generated a unique inflammatory response lacking distinct microglia and astrocytes rich zones, moreover, the inflammatory cell numbers and the breadth of the inflammatory response is further reduced as compared to the control and E9-coated catheters.

FIG. 1 is a graph of cell counts, obtained at 100-μm intervals from the catheter tract and normalized for cubic area are plotted with standard deviations presented as above/below error bars. Note that at distances beyond 1 cm ($10^{th}$ 100-μm interval) there is a significant difference between the immune response to the control catheter and the E9- and RZA15-coated catheters, with the RZA15-coated catheters in particular demonstrating reduced cell numbers reflective of an attenuated immune response.

Conclusions from Initial Study of Anti-Inflammatory Coatings on Clinical Grade PDMS Ventricular Catheters Analysis of the catheter surface chemistry shows that the anti-inflammatory small molecule coatings can be applied to the clinical grade ventricular catheters in a conformal fashion. Moreover, the analysis of the rabbit brain parenchyma immune response to these coated devices demonstrated marked reductions in inflammatory cells around the catheter tracts of E9- and RZA15-coated catheters, providing strong support for further testing of these coatings for intracranial applications.

These coatings are causing tissue microglia to remain in a resting state phenotype so that they will not produce the pro-inflammatory cytokines that promote astrocyte recruitment and activation. This should cause significant reductions in CSF shunt failure rates, as well as be useful in broader CNS applications. For example, implanted penetrating cortical electrode arrays used for recording neuronal action potentials are currently hampered by the fact that within 2 years of implantation they can no longer record neuronal firing because of progressive invasion of microglia and astrocytes. Therefore, these coatings also have the potential to significantly improve electrode array longevity.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A central nervous system implant having bound to one or more surfaces thereof a small molecule comprising a chemical moiety of Formula XII or at least one polymer comprising the chemical moiety of Formula XII, wherein the chemical moiety of Formula XII is in an effective amount to reduce inflammation mediated by microglia cells and/or astrocytes, wherein Formula XII has the formula:

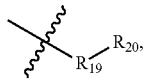

Formula XII wherein, $R_{19}$ is —NR—, —O—, —S—, —C(O)NH—, —C(O)O—, —NHC(O)—, —OC(O)—, —NH—NHC(O)—, —OC(O)NH—, —NHC(O)O—, —C(O)—, —OC(O)O—, —S(=O_2)_2—, —S(=O)—, —N=N—, or —N=CH—, wherein Rx is hydrogen, unsubstituted alkyl, substituted alkyl, unsubstituted alkenyl, substituted alkenyl, unsubstituted alkynyl, substituted alkynyl, unsubstituted aryl, substituted aryl, unsubstituted heteroaryl, or substituted heteroaryl, $R_{20}$ has the structure:

—Az—Bz—(—Cz)δ,      Formula XIII wherein δ is 1,
Az is

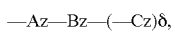

Formula XIV wherein in Formula XIV of Az: $R_{31}$ is —$(CR_{32}R_{32})_p$—, p is an integer from 0 to 5, each $R_{32}$ is hydrogen, unsubstituted alkyl, or substituted alkyl, each $R^e$ is independently unsubstituted alkyl, substituted alkyl, unsubstituted alkenyl, substituted alkenyl, unsubstituted alkynyl, substituted alkynyl, unsubstituted alkoxy, substituted alkoxy, unsubstituted alkylamino, substituted alkylamino, unsubstituted dialkylamino, substituted dialkylamino, hydroxy, unsubstituted aryl, substituted aryl, unsubstituted heteroaryl, substituted heteroaryl, unsubstituted carboxyl, substituted carboxyl, unsubstituted amino, substituted amino, unsubstituted amido, substituted amido, unsubstituted $C_3$-$C_{20}$ cyclic, substituted $C_3$-$C_{20}$ cyclic, unsubstituted $C_3$-$C_{20}$ heterocyclic, or substituted $C_3$-$C_{20}$ heterocyclic, y is an integer between 0 and 11, inclusive, R25, $R_{26}$, $R_{27}$, $R_{28}$, $R_{29}$, and $R_{30}$ are independently C or N, wherein the bonds between adjacent $R_{25}$ to $R_{30}$ are double or single according to valency, and wherein $R_{25}$ to $R_{30}$ are bound to none, one, or two hydrogens according to valency, or Az is

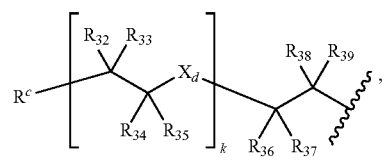

Formula XV wherein in Formula XV of Az, $R_{32}$, $R_{33}$, $R_{34}$, $R_{35}$, $R_{36}$, $R_{37}$, $R_{38}$, and $R_{39}$ are independently hydrogen, unsubstituted alkyl, substituted alkyl, unsubstituted alkenyl, substituted alkenyl, unsubstituted alkynyl, substituted alkynyl, unsubstituted phenyl, substituted phenyl, unsubstituted aryl, substituted aryl, unsubstituted heteroaryl, substituted heteroaryl, unsubstituted arylalkyl, substituted arylalkyl, unsubstituted alkoxy, substituted alkoxy, unsubstituted aroxy, substituted aroxy, unsubstituted carbonyl, substituted carbonyl, unsubstituted carboxyl, substituted carboxyl, unsubstituted amino, substituted amino, unsubstituted amido, substituted amido, unsubstituted $C_3$-$C_{20}$ cyclic, substituted $C_3$-$C_{20}$ cyclic, unsubstituted $C_3$-$C_{20}$ heterocyclic, substituted $C_3$-$C_{20}$ heterocyclic, poly(ethylene glycol), or poly(lactic-co-glycolic acid), k is an integer from 0 to 20, each $X_d$ is independently absent, O, or S, and $R^c$ is Bz, wherein Bz is

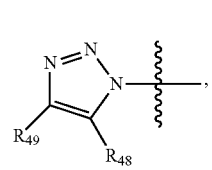

Formula XVII wherein $R_{48}$ and $R_{49}$ are independently hydrogen,

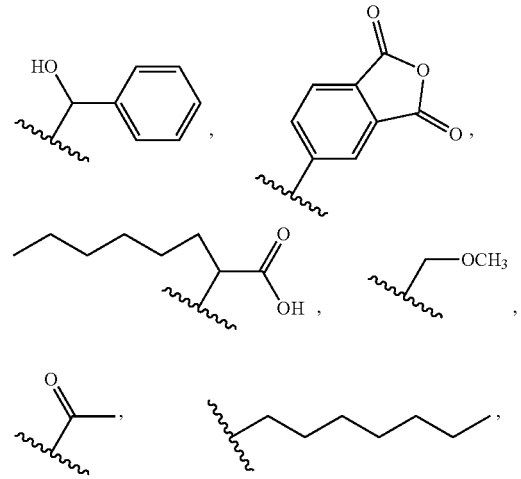

or

Cz, and wherein Cz is

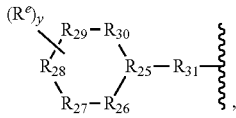

Formula XIV wherein in Formula XIV of Cz, $R_{31}$ is —$(CR_{32}R_{32})_p$— or —$(CR_{32}R_{32})_p$—Xb—$(CR_{32}R_{32})_q$—, p and q are independently integers between 0 to 5, inclusive, each $R_{32}$ is hydrogen, unsubstituted alkyl, or substituted alkyl, $X_b$ is absent, —O—, —S—, —S(O)—, —S(O)$_2$—, or $NR_{47}$, $R_{47}$ is unsubstituted alkyl or substituted alkyl, each $R^e$ is independently unsubstituted alkyl, substituted alkyl, unsubstituted alkenyl, unsubstituted alkenyl, unsubstituted alkynyl, substituted alkynyl, unsubstituted alkoxy, substituted alkoxy, unsubstituted alkylamino, substituted alkylamino, unsubstituted dialkylamino, substituted dialkylamino, hydroxy, unsubstituted aryl, substituted aryl, unsubstituted heteroaryl, substituted heteroaryl, unsubstituted carboxyl, substituted carboxyl, unsubstituted amino, substituted amino, unsubstituted amido, substituted amido, unsubstituted $C_3$-$C_{20}$ cyclic, substituted $C_3$-$C_{20}$ cyclic, unsubstituted $C_3$-$C_{20}$ heterocyclic, or substituted $C_3$-$C_{20}$ heterocyclic, y is an integer between 0 and 11, inclusive, wherein (i) $R_{25}$, $R_{26}$, $R_{27}$, $R_{28}$, $R_{29}$, and $R_{30}$ are independently C or N, wherein the bonds between adjacent $R_{25}$ to $R_{30}$ are double or single according to valency, and wherein $R_{25}$ to $R_{30}$ are bound to none, one, or two hydrogens according to valency, (ii) $R_{25}$, $R_{26}$, $R_{27}$, $R_{28}$, $R_{29}$, and $R_{30}$ form a thiomorpholine-1,1-dioxide moiety, or (iii) $R_{25}$, $R_{26}$, $R_{27}$, $R_{28}$, $R_{29}$, and $R_{30}$ form a tetrahydropyran.

2. The central nervous system implant of claim 1, wherein for Formula XIV of Az, each $R_{32}$ is hydrogen, p is 1, $R_{25}$ is C, and $R_{26}$-$R_{30}$ are CH, and the bonds between $R_{25}$ and $R_{26}$, between $R_{27}$ and $R_{28}$, and between $R_{29}$ and $R_{30}$ are double bonds, y is 1, and $R^e$ is Bz having Formula XVII.

3. The central nervous system implant of claim 1, wherein for Formula XIV of Az, each $R_{32}$ is hydrogen, p is 1, $R_{25}$ is C, and $R_{26}$-$R_{30}$ are CH, and the bonds between $R_{25}$ and $R_{26}$, between $R_{27}$ and $R_{28}$, and between $R_{29}$ and $R_{30}$ are double bonds, y is 1, and wherein $R_{48}$ and $R_{49}$ are not both hydrogen.

4. The central nervous system implant of claim 3, wherein for Formula XIV of Cz, $R_{31}$ is —$(CR_{32}R_{32})_p$—$X_b$—$(CR_{32}R_{32})_q$—, each $R_{32}$ is hydrogen, and p is 0.

5. The central nervous system implant of claim 4, wherein Formula XIV of Cz is

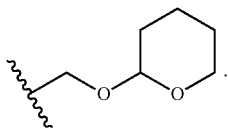 [SMILES: *COC1CCCCO1]

6. The central nervous system implant of claim 1, wherein Az is

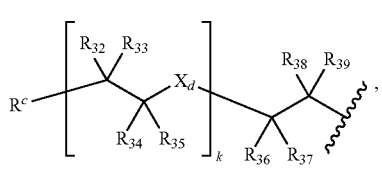

Formula IX and $R^c$ is Bz having Formula XVII.

7. The central nervous system implant of claim 6, wherein for Formula IX of Az, Xd is O, and $R_{32}$-$R_{39}$ are hydrogen.

8. The central nervous system implant of claim 6, wherein $R_{48}$ and $R_{49}$ are not both hydrogen.

9. The central nervous system implant of claim 8, wherein for Formula XIV of Cz is

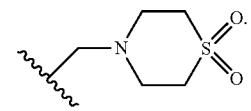

10. The central nervous system implant of claim 8, wherein for Formula XIV of Cz, $R_{31}$ is —$(CR_{32}R_{32})_p$—, each $R_{32}$ is hydrogen, p is 0, $R_{25}$ is C, $R_{26}$-$R_{30}$ are CH, and the bonds between $R_{25}$ and $R_{26}$, between $R_{27}$ and $R_{28}$, and between $R_{29}$ and $R_{30}$ are double bonds.

11. The central nervous system implant of claim 8, wherein Formula XIV of Cz is

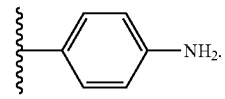 [SMILES: *c1ccc(N)cc1]

12. The central nervous system implant of claim 1, wherein the chemical moiety is selected from the group consisting of

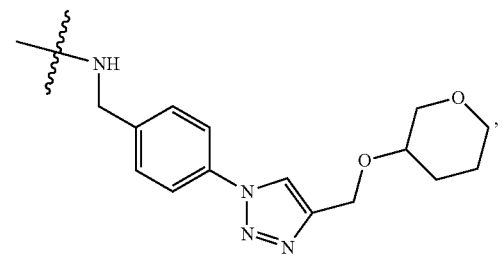

E9 (Z2-Y12)

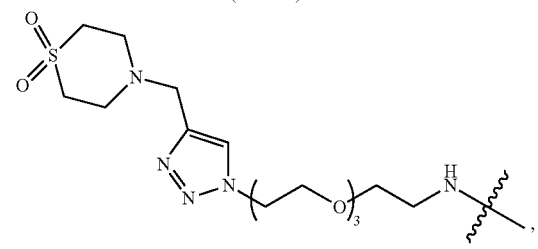

RZA (ZI-Y15)

-continued

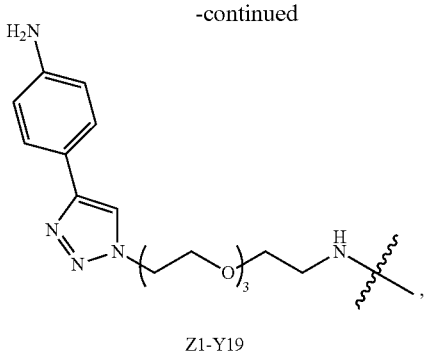

Z1-Y19 and combinations thereof.

13. A central nervous system implant formed from or having a coating comprising a material having bound thereto a chemical moiety of Formula XII in an effective amount to reduce inflammation mediated by microglia cells and/or astrocytes, wherein the chemical moiety of Formula XII has the formula:

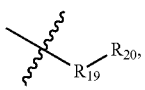

Formula XII wherein, $R_{19}$ is —NRx—, —O—, —S—, —C(O)NH—, —C(O)O—, —NHC(O)—, —OC(O)—, —NH—NHC(O)—, —OC(O)NH—, —NHC(O)O—, —C(O)—, —OC(O)O—, —S(=O$_2$)$_2$—, —S(=O)—, —N=N—, or —N=CH—, wherein Rx is hydrogen, unsubstituted alkyl, substituted alkyl, unsubstituted alkenyl, substituted alkenyl, unsubstituted alkynyl, substituted alkynyl, unsubstituted aryl, substituted aryl, unsubstituted heteroaryl, or substituted heteroaryl, $R_{20}$ has the structure:

—Az—Bz—(—Cz)δ,  Formula XIII wherein δ is 1,

Az is

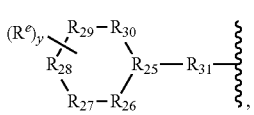

Formula XIV wherein in Formula XIV of Az: $R_{31}$ is —(CR$_{32}$R$_{32}$)$_p$—, p is an integer from 0 to 5, each $R_{32}$ is hydrogen, unsubstituted alkyl, or substituted alkyl, each $R^e$ is independently unsubstituted alkyl, substituted alkyl, unsubstituted alkenyl, unsubstituted alkenyl, unsubstituted alkynyl, substituted alkynyl, unsubstituted alkoxy, substituted alkoxy, unsubstituted alkylamino, substituted alkylamino, unsubstituted dialkylamino, substituted dialkylamino, hydroxy, unsubstituted aryl, substituted aryl, unsubstituted heteroaryl, substituted heteroaryl, unsubstituted carboxyl, substituted carboxyl, unsubstituted amino, substituted amino, unsubstituted amido, substituted amido, unsubstituted $C_3$-$C_{20}$ cyclic, substituted $C_3$-$C_{20}$ cyclic, unsubstituted $C_3$-$C_{20}$ heterocyclic, or substituted $C_3$-$C_{20}$ heterocyclic, y is an integer between 0 and 11, inclusive, $R_{25}$, $R_{26}$, $R_{27}$, $R_{28}$, $R_{29}$, and $R_{30}$ are independently C or N, wherein the bonds between adjacent $R_{25}$ to $R_{30}$ are double or single according to valency, and wherein $R_{25}$ to $R_{30}$ are bound to none, one, or two hydrogens according to valency, or Az is

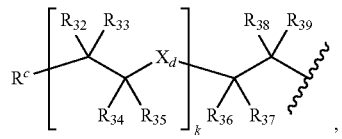

Formula XV wherein in Formula XV of Az, $R_{32}$, $R_{33}$, $R_{34}$, $R_{35}$, $R_{36}$, $R_{37}$, $R_{38}$, and $R_{39}$ are independently hydrogen, unsubstituted alkyl, substituted alkyl, unsubstituted alkenyl, substituted alkenyl, unsubstituted alkynyl, substituted alkynyl, unsubstituted phenyl, substituted phenyl, unsubstituted aryl, substituted aryl, unsubstituted heteroaryl, substituted heteroaryl, unsubstituted arylalkyl, substituted arylalkyl, unsubstituted alkoxy, substituted alkoxy, unsubstituted aroxy, substituted aroxy, unsubstituted carbonyl, substituted carbonyl, unsubstituted carboxyl, substituted carboxyl, unsubstituted amino, substituted amino, unsubstituted amido, substituted amido, unsubstituted $C_3$-$C_{20}$ cyclic, substituted $C_3$-$C_{20}$ cyclic, unsubstituted $C_3$-$C_{20}$ heterocyclic, substituted $C_3$-$C_{20}$ heterocyclic, poly(ethylene glycol), or poly(lactic-co-glycolic acid), k is an integer from 0 to 20, each $X_d$ is independently absent, O, or S, and $R^e$ is Bz, wherein Bz is

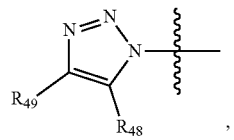

Formula XVII wherein $R_{48}$ and $R_{49}$ are independently hydrogen,

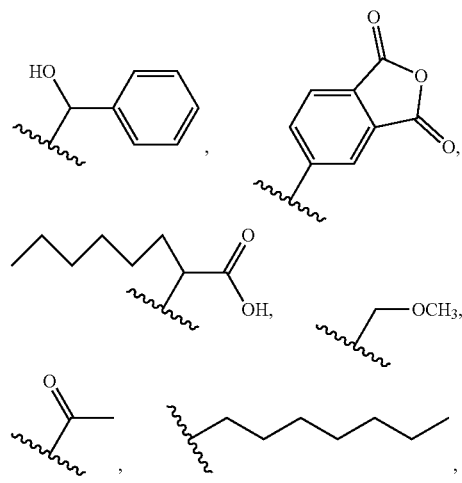

or

Cz, and wherein Cz is

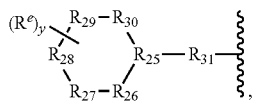

Formula XIV wherein in Formula XIV of Cz, $R_{31}$ is —$(CR_{32}R_{32})_p$— or —$(CR_{32}R_{32})_p$—$X_b$—$(CR_{32}R_{32})_q$—, p and q are independently integers between 0 to 5, inclusive, each $R_{32}$ is hydrogen, unsubstituted alkyl, or substituted alkyl, $X_b$ is absent, —O—, —S—, —S(O)—, —S(O)$_2$—, or $NR_{47}$, $R_{47}$ is unsubstituted alkyl or substituted alkyl, each $R^e$ is independently unsubstituted alkyl, substituted alkyl, unsubstituted alkenyl, substituted alkenyl, unsubstituted alkynyl, substituted alkynyl, unsubstituted alkoxy, substituted alkoxy, unsubstituted alkylamino, substituted alkylamino, unsubstituted dialkylamino, substituted dialkylamino, hydroxy, unsubstituted aryl, substituted aryl, unsubstituted heteroaryl, substituted heteroaryl, unsubstituted carboxyl, substituted carboxyl, unsubstituted amino, substituted amino, unsubstituted amido, substituted amido, unsubstituted $C_3$-$C_{20}$ cyclic, substituted $C_3$-$C_{20}$ cyclic, unsubstituted $C_3$-$C_{20}$ heterocyclic, or substituted $C_3$-$C_{20}$ heterocyclic, y is an integer between 0 and 11, inclusive, wherein (i) $R_{25}$, $R_{26}$, $R_{27}$, $R_{28}$, $R_{29}$, and $R_{30}$ are independently C or N, wherein the bonds between adjacent $R_{25}$ to $R_{30}$ are double or single according to valency, and wherein $R_{25}$ to $R_{30}$ are bound to none, one, or two hydrogens according to valency, (ii) $R_{25}$, $R_{26}$, $R_{27}$, $R_{28}$, $R_{29}$, and $R_{30}$ form a thiomorpholine-1,1-dioxide moiety, or (iii) $R_{25}$, $R_{26}$, $R_{27}$, $R_{28}$, $R_{29}$, and $R_{30}$ form a tetrahydropyran.

14. The central nervous system implant of claim 13, wherein for Formula XIV of Az, each $R_{32}$ is hydrogen, p is 1, $R_{25}$ is C, and $R_{26}$-$R_{30}$ are CH, and the bonds between $R_{25}$ and $R_{26}$, between $R_{27}$ and $R_{28}$, and between $R_{29}$ and $R_{30}$ are double bonds, y is 1, and $R^e$ is Bz having Formula XVII.

15. The central nervous system implant of claim 13, wherein for Formula XIV of Az, each $R_{32}$ is hydrogen, p is 1, $R_{25}$ is C, and $R_{26}$-$R_{30}$ are CH, and the bonds between $R_{25}$ and $R_{26}$, between $R_{27}$ and $R_{28}$, and between $R_{29}$ and $R_{30}$ are double bonds, y is 1, and wherein $R_{48}$ and $R_{49}$ are not both hydrogen.

16. The central nervous system implant of claim 15, wherein for Formula XIV of Cz, $R_{31}$ is —$(CR_{32}R_{32})_p$—$X_b$—$(CR_{32}R_{32})_q$—, each $R_{32}$ is hydrogen, and p is 0.

17. The central nervous system implant of claim 16, wherein Formula XIV of Cz is

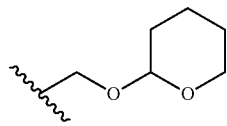

18. The central nervous system implant of claim 13, wherein Az is

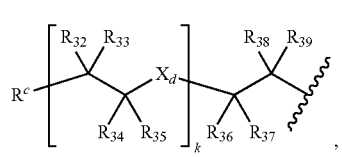

Formula IX and $R^c$ is Bz having Formula XVII.

19. The central nervous system implant of claim 18, wherein for Formula IX of Az, Xd is O, and $R_{32}$-$R_{39}$ are hydrogen.

20. The central nervous system implant of claim 18, wherein $R_{48}$ and $R_{49}$ are not both hydrogen.

21. The central nervous system implant of claim 20, wherein Formula XIV of Cz is

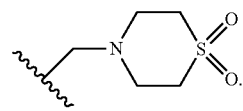 [SMILES: *CN1CCS(=O)(=O)CC1]

22. The central nervous system implant of claim 20, wherein for Formula XIV of Cz, $R_{31}$ is —$(CR_{32}R_{32})_p$—, each $R_{32}$ is hydrogen, p is 0, $R_{25}$ is C, $R_{26}$-$R_{30}$ are CH, and the bonds between $R_{25}$ and $R_{26}$, between $R_{27}$ and $R_{28}$, and between $R_{29}$ and $R_{30}$ are double bonds.

23. The central nervous system implant of claim 20, wherein Formula XIV of Cz is

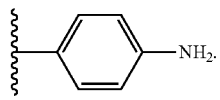

24. The central nervous system implant of claim 13, wherein the chemical moiety is selected from the group consisting of

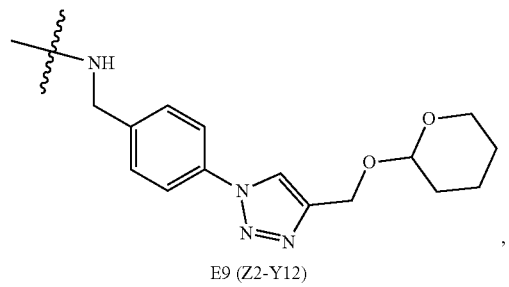

E9 (Z2-Y12)

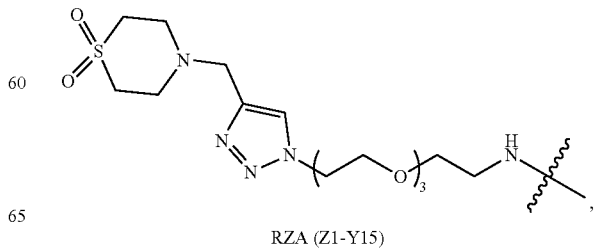

RZA (Z1-Y15)

-continued

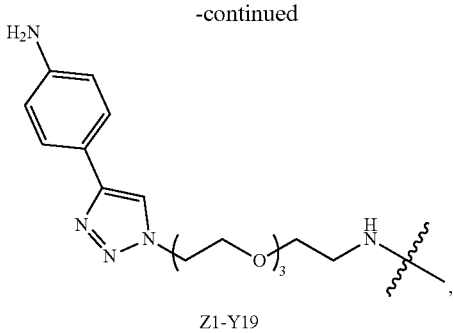

Z1-Y19 and combinations thereof.

25. The central nervous system implant of claim 13, wherein the chemical moiety is functionalized on a polymer selected from the group consisting of poly(dimethylsiloxane), poly(lactone), poly(olefins), poly(anhydride), poly(urethane), poly(acrylates), poly(orthoester), poly(ethers), poly(esters), poly(phosphazine), poly(ether ester)s, poly(amino acids), synthetic poly(amino acids), poly(carbonates), poly(hydroxyalkanoate)s, zwitterionic polymers, gelatin, collagen, blends thereof, and copolymers thereof.

26. The central nervous system implant of claim 1, wherein the neurological implant is selected from the group consisting of a neurological shunt, cortical electrode array, neurological leads, microdialysis sampling probe, carbon fiber/microwire-based microfabrication-based probes for voltammetry, carbon fiber/microwire-based microfabrication-based probes for electrophysiological recording, electrochemical device, implantable sensors, neurostimulator, and orthopedic implants that are placed adjacent to or in abutment with nerves, and pacemaker leads.

27. A method of making the central nervous system implant of claim 1 comprising:
coating a central nervous system implant with the small molecule comprising the chemical moiety of Formula XII and/or the at least one polymer comprising the chemical moiety of Formula XII to form a coating covalently or non-covalently bound to one or more surfaces of the central nervous system implant.

28. The method of claim 27, wherein the coating is carried out by spray coating, dip coating, brush coating or combinations thereof.

29. A method of making the central nervous system implant of claim 1 comprising the steps of:
(a) providing the at least one polymer comprising the chemical moiety of Formula XII, and
(b) forming all or a part of the central nervous system implant from the at least one polymer comprising the chemical moiety of Formula XII.

30. The method of claim 29, wherein the chemical moiety is selected from the group consisting of

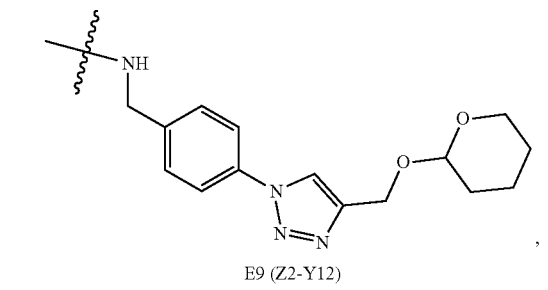

E9 (Z2-Y12)

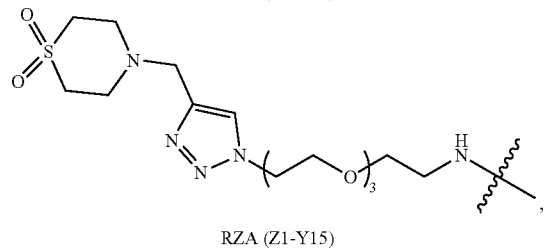

RZA (Z1-Y15)

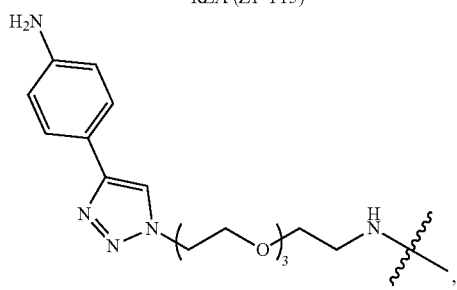

Z1-Y19 and combinations thereof.

31. A method of decreasing inflammation of central nervous system tissue adjacent to a central nervous system implant comprising implanting the central nervous system implant of claim 1 into or adjacent to or in abutment with the central nervous system tissue.

* * * * *